United States Patent
Schoenfisch et al.

(10) Patent No.: US 8,399,005 B2
(45) Date of Patent: Mar. 19, 2013

(54) USE OF NITRIC OXIDE TO ENHANCE THE EFFICACY OF SILVER AND OTHER TOPICAL WOUND CARE AGENTS

(75) Inventors: Mark H. Schoenfisch, Chapel Hill, NC (US); Evan M. Hetrick, Indianapolis, IN (US); Nathan A. Stasko, Durham, NC (US); C. Bryce Johnson, John's Island, SC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 141 days.

(21) Appl. No.: 12/682,305

(22) PCT Filed: Oct. 10, 2008

(86) PCT No.: PCT/US2008/079582
§ 371 (c)(1),
(2), (4) Date: Jul. 7, 2010

(87) PCT Pub. No.: WO2009/049208
PCT Pub. Date: Apr. 16, 2009

(65) Prior Publication Data
US 2010/0297200 A1 Nov. 25, 2010

Related U.S. Application Data

(60) Provisional application No. 60/998,740, filed on Oct. 12, 2007.

(51) Int. Cl.
*A01N 25/28* (2006.01)
*A01N 59/16* (2006.01)

(52) U.S. Cl. ........ 424/417; 424/406; 424/421; 424/423; 424/427; 424/430; 424/434; 424/489; 424/490; 424/618; 424/718

(58) Field of Classification Search .................. None
See application file for complete search history.

(56) References Cited

U.S. PATENT DOCUMENTS
6,896,899 B2   5/2005   Demopoulos et al.
(Continued)

FOREIGN PATENT DOCUMENTS
WO   WO 02/20026 A   3/2002
(Continued)

OTHER PUBLICATIONS

Bohl Masters, K.S., et al., "Effects of Nitric Oxide Releasing Poly-(vinyl alcohol) Hydrogel Dressings on Dermal Wound Healing in Diabetic Mice", *Wound Repair and Regeneration*, vol. 10, No. 5 (Jan. 1, 2002), pp. 286-204.

(Continued)

*Primary Examiner* — Neil Levy
(74) *Attorney, Agent, or Firm* — Alston & Bird LLP

(57) ABSTRACT

The present invention is directed to compositions comprising at least one nitric oxide donor and at least one second therapeutically active agent with antimicrobial or wound healing capability. In one embodiment, the nitric oxide donor is a nanoparticle which is designed to control for the amount and duration of release of nitric oxide. The nanoparticle may further comprise the additional therapeutically active agent. The composition is useful for enhancing wound healing and for treating and preventing microbial infection. In one embodiment, the composition is directed toward reducing oral bacteria or dental plaque. The combination of one or more nitric oxide donors and one or more additional therapeutically active agent results in unexpected synergistic effects, wherein both the antimicrobial efficacy of the nitric oxide and the antimicrobial or wound healing efficacy of the second therapeutically active agent are enhanced. As a result, a patient may benefit from reduced dosage requirements and a reduced likelihood of antimicrobial resistance. The composition may be formulated for local or systemic administration, for topical applications as well as for use in coatings for medical supplies and devices.

19 Claims, 6 Drawing Sheets

A – implantable biomaterial, biomedical implant, indwelling medical device
B – nitric oxide-generating layer (containing a NO-donor, small molecule NO-donor, and/or NO-donating macromolecule)
C – antimicrobial-, growth factor-, and/or wound healing-eluting layer (e.g., silver, antibiotic, antibody, etc.)
NO = nitric oxide   X = antimicrobial, growth factor, and/or wound healing agent

U.S. PATENT DOCUMENTS

| | | | |
|---|---|---|---|
| 2002/0115586 A1 | 8/2002 | Enikolopov | |
| 2005/0249818 A1* | 11/2005 | Sawan et al. | 424/618 |
| 2006/0159726 A1 | 7/2006 | Shell | |
| 2007/0086954 A1 | 4/2007 | Miller | |
| 2007/0129690 A1* | 6/2007 | Rosenblatt et al. | 604/265 |
| 2009/0214618 A1* | 8/2009 | Schoenfisch et al. | 424/426 |

FOREIGN PATENT DOCUMENTS

| | | | |
|---|---|---|---|
| WO | WO 2004/087212 A | | 10/2004 |
| WO | WO 2006/084914 A | | 8/2006 |
| WO | WO 2006/100155 A | | 9/2006 |
| WO | WO 2006/128121 A | | 11/2006 |
| WO | WO 2006/128743 | * | 12/2006 |
| WO | WO 2007/057763 A | | 5/2007 |
| WO | WO 2007/084533 A | | 7/2007 |
| WO | WO 2007/100910 A | | 9/2007 |

OTHER PUBLICATIONS

Dobmeier, Kevin P., et al., "Antibacterial Properties of Nitric Oxide-Releasing Sol-Gel Microarrays", *Biomacromolecules*, vol. 5, No. 6, (Nov. 1, 2004), pp. 2493-2495.

Hetrick, et al, "Antibacterial Nitric Oxide-Releasing Xerogels: Cell Viability and Parallel Plate Flow Cell Adhesion Studies", *Biomaterials*, Elsevier Science Publishers, vol. 28, No. 11 (Jan. 31, 2007), pp. 1948-1956.

Hetrick, E.M., et al., "Reducing Implant-Related Infections: Active Release Strategies", *Chem. Soc. Rev*, vol. 36, (2006), pp. 780-789.

Nablo, B.J. et al., "Nitric Oxide-Releasing Sol-Gels as Antibacterial Coatings for Orthopedic Implants", *Biomaterials*, Elsevier Science Publishers, vol. 26, No. 8 (Mar. 1, 2005), pp. 917-924.

Nablo, et al., "Inhibition of Implant-Associated Infections via Nitric Oxide Release", *Biomaterials*, Elsevier Science Publishers, vol. 26, No. 34 (Dec. 1, 2005), pp. 6984-6990.

* cited by examiner

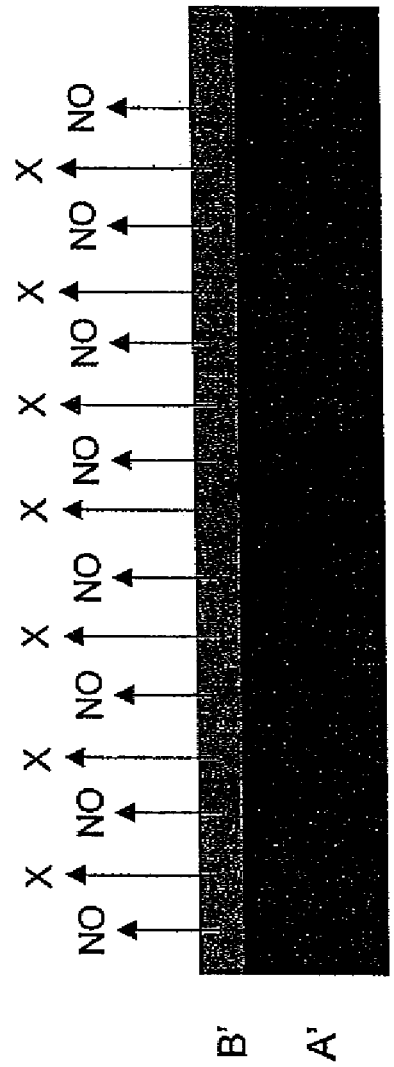

A' – implantable biomaterial, biomedical implant, indwelling medical device

B' – coating the releases/elutes both nitric oxide (contains a NO-donor, small molecule NO-donor, and/or macromolecular NO-donor) and one or more other antimicrobial agents, growth factors, and/or wound healing agents (e.g., silver, antibiotic, antibody, etc.)

NO = nitric oxide   X = antimicrobial, growth factor, and/or wound healing agent

Figure 2

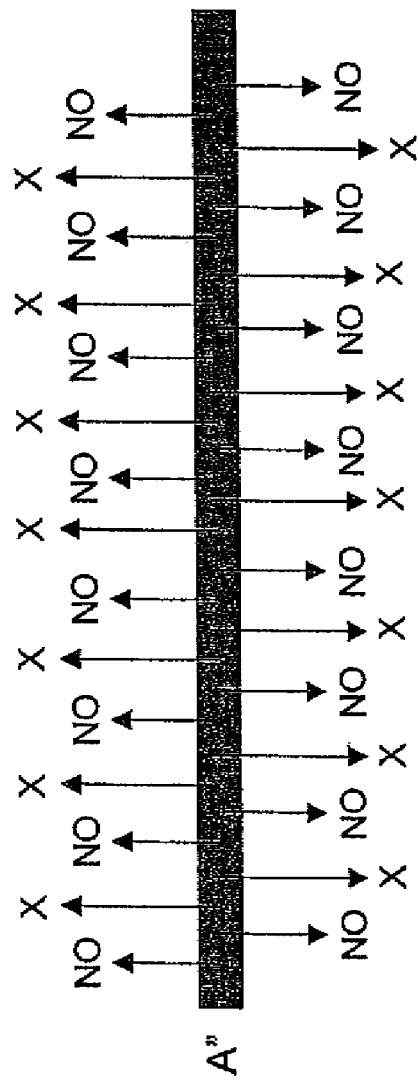

A" – wound dressing, wound barrier, barrier dressing, biomedical implant, indwelling medical device, biomaterial, hydrogel, matrix, cream, foam, ointment, gel, etc. that releases/elutes both nitric oxide (contains a NO-donor, small molecule NO-donor, and/or macromolecular NO-donor) and one or more other antimicrobial agents, growth factors, and/or wound healing agents (e.g., silver, antibiotic, antibody, etc.)

NO = nitric oxide    X = antimicrobial, growth factor, and/or wound healing agent

Figure 3

USE OF NITRIC OXIDE TO ENHANCE THE EFFICACY OF SILVER AND OTHER TOPICAL WOUND CARE AGENTS

FEDERALLY SPONSORED RESEARCH OR DEVELOPMENT

This invention was made with United States Government support under Grant Number EB000708 awarded by the National Institute of Health. The United States Government has certain rights in the invention.

TECHNICAL FIELD

The presently disclosed subject matter relates to the combined administration of nitric oxide and a second therapeutically active agent, such as an antimicrobial or wound healing agent and to compositions thereof.

BACKGROUND

Endogenously produced nitric oxide (NO) is believed to produce a variety of effects in vivo, including reducing inflammation, regulating blood flow, and fighting microbial infection. Exogenously provided NO gas has also been described in the treatment of infection, to prevent biofilm formation, to increase the rate of wound re-epithelialization, and to rapidly close diabetic foot ulcers.

The potential therapeutic usefulness of NO has led to the search for solid-phase nitric oxide donors, including those capable of controlled NO release. See Keefer, L. K., *Chemtech* 28, 30-35 (1998). Several small molecule NO donors have been reported, the most notable being N-diazeniumdiolates. For example, small molecule N-diazeniumdiolate NO donors can be synthesized by the reaction of amines with NO at elevated pressure and have been used, for example, to spontaneously generate NO in aqueous solution. See Hrabie, J. A. and Keefer, L. K., *Chem. Rev.* 102, 1135-1154 (2002).

Macromolecular NO-releasing scaffolds have also been described, including NO-releasing dendrimers (see Stasko, N. A., and Schoenfisch, M. H., *J. Am. Chem. Soc.* 128, 8265-8271 (2006)), NO-releasing gold nanoparticles (see Rothrock, A. R., et al., *J. Am. Chem. Soc.* 127, 9362-9363 (2005)), and NO-releasing silica nanoparticles. See Shin J. H. et al., *J. Am. Chem. Soc.* 129, 4612-4619 (2007). A recent report describes the antibacterial activity of NO-releasing xerogel film. See Hetrick, E. M. and Schoenfisch, M. H., *Biomaterials* 28, 1948-1956 (2007).

Antibiotic resistance has caused bacterial infections to become the most common cause of infectious disease-related death. See Robson, M. C. (1977) *Surg. Clin. N. Am.* 77, 637-650. Antibiotic-resistant pathogens are the primary reason for a majority of all lethal nosocomial infections. The growing danger of life-threatening infections and the rising economic burden of resistant bacteria have created a demand for new antibacterial therapeutics. The present invention provides a new therapy for the treatment of microbial infections.

SUMMARY

Compositions and methods for treating or preventing microbial infections and for promoting wound healing are provided. The compositions comprise at least one nitric oxide (NO) donor and at least one therapeutically active agent. The therapeutically active agent is selected from an antimicrobial agent, an antiviral agent, a wound healing agent, a wound care agent, a growth factor, an antibody, and other biological agents. While any NO donor can be utilized, in one embodiment the donor is a nanoparticle that is designed to control for the amount and duration of release of nitric oxide. The nanoparticle may additionally comprise the therapeutically active agent. As indicated, the methods are useful for treating or preventing microbial infections, for reducing implant-related infections, and for promoting wound healing. The methods comprise the combined administration of at least one NO donor and at least one therapeutically active agent. The combination of one or more NO donor and one or more therapeutic agent results in unexpected synergistic effects, wherein both the antimicrobial efficacy of the nitric oxide and the antimicrobial or wound healing efficacy of the second therapeutic agent are enhanced. As a result, a patient may benefit from reduced dosage requirements and a reduced likelihood of antimicrobial resistance.

BRIEF DESCRIPTION OF THE FIGURES

Reference is made to the accompanying figures in which are shown illustrative embodiments of the presently disclosed subject matter.

FIG. 2 illustrates an embodiment related to implantable biomaterial, biomedical implant, or indwelling medical device A' that comprises layer B' which can release both NO and therapeutic agent X.

FIG. 3 illustrates composition A" (e.g., a wound dressing, wound barrier, barrier dressing, biomedical implant, a biomaterial, hydrogel, matrix, cream, foam, ointment, or gel) that releases both NO and X.

DETAILED DESCRIPTION

Figure 1:
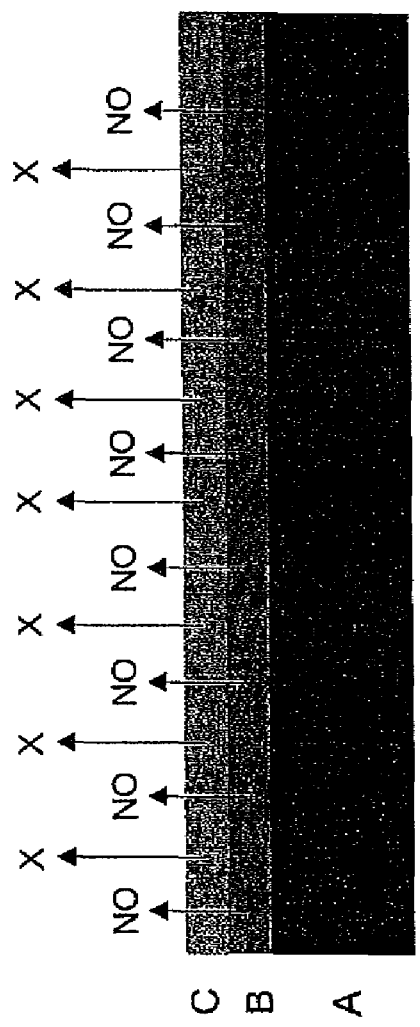
FIG. 1 illustrates an embodiment related to implantable biomaterial, biomedical implant, or indwelling medical device A' that comprises NO-releasing layer B and therapeutic agent-releasing layer C, which releases therapeutic agent X.

The presently disclosed subject matter relates to the synergistic effects related to the combined administration of nitric oxide (NO) and a second therapeutically active agent. The present invention provides compositions comprising at least one nitric oxide donor and at least one second therapeutically active agent. The therapeutically active agent may be an antimicrobial agent, an antiviral agent, a wound healing agent, a growth factor, an antibody, or other biological or therapeutic agent. The presently disclosed subject matter also pertains to the use of NO to enhance the antimicrobial efficacy of silver and other commonly used wound care agents, including, but not limited to antibacterials, growth factors, and other biological wound healing agents, as well as the ability of such agents to enhance the antimicrobial efficacy of NO.

The compositions and methods of the invention are useful for the treatment, inhibition, and prevention of microbial infections; treating, reducing, or preventing oral bacteria and dental plaque; preventing, treating, or reducing implant-related infections; sterilizing medical implants, and the like. NO can be used as a suitable addition to topical antibacterial agents. This combination is useful in cases from burns to ulcers to cuts and other wounds. In some embodiments, the pharmaceutical compositions of the invention include therapeutically effective amounts of at least one nitric oxide donor and at least one therapeutically active agent. The methods comprise administering to a subject in need thereof at least one nitric oxide donor in combination with at least one therapeutically active agent.

As indicated, the present invention is related to the combined administration of at least one NO donor and at least one second therapeutically active agent. The compositions and methods of the invention are based upon the discovery that NO when used in combination with a second therapeutic agent is capable of enhancing the effects of the second therapeutic agent. Thus, the compositions and methods are useful for treating and preventing bacterial and viral infection, particularly for pathogenic bacteria, more particularly for gram-positive strains and those that exhibit resistance to conventional antibiotics.

NO is a biocide and possesses broad spectrum antibacterial activity. It shuts down many metabolic pathways. The effects of NO have been shown to be indirect, via formation of oxidative (e.g., $ONOO^-$) or nitrosative (e.g., $N_2O_3$) species that target bacterial DNA and proteins or via direct reaction with transition metal centers. NO directly disrupts zinc metalloproteins and iron-sulfur clusters, inhibiting replication and inducing toxic oxidizing reactions.

The nitric oxide donor and the therapeutically active agent may be contained within a single composition or alternatively may be administered concurrently or sequentially (consecutively) in any order. For sequential administration, each of the NO donor and the therapeutic agent can be formulated in its own pharmaceutical composition, each of which is to be administered sequentially, in any order. Alternatively, the NO donor and the therapeutic agent can be formulated together. The compositions may be formulated for oral, systemic, topical, intravenous, intraparenteral, intravaginal, intraocular, transbuccal, transmucosal, or transdermal administration.

In some embodiments, the present invention involves a pharmaceutical composition comprising one or more nitric oxide donors and one or more therapeutic agents. The nitric oxide donor is a moiety that can donate, release, directly or indirectly transfer, stimulate the endogenous production of, or elevate endogenous levels of, any form of nitrogen monoxide. The therapeutic agent is a compound for use in treating or preventing bacterial, viral, or microbial infections or for enhancing wound healing. The nitric oxide donor and the therapeutic agent may exhibit synergistic effects when used together.

The invention also relates to a method of treating or preventing microbial infection in an individual. The method comprises administering to the individual one or more nitric oxide donors and one or more therapeutic agents, wherein the nitric oxide donor is a moiety that can donate, release, directly or indirectly transfer, stimulate the endogenous production of, or elevate endogenous levels of, any form of nitrogen monoxide, and wherein the therapeutic agent is a compound for use in treating or preventing bacterial, viral, or microbial infections. In one embodiment, the administration of the nitric oxide donor and the therapeutic agent provides an antimicrobial activity similar to or greater than that related to administration of a higher dosage of the therapeutic agent in the absence of administration of the nitric oxide donor. In another embodiment, administration provides a reduced likelihood of antimicrobial resistance developing to the therapeutic agent. In still another embodiment, administration provides the ability to achieve the desired antimicrobial effect by administering a lower dose of therapeutic agent, including but not limited to below the systemic or local toxicity level of the therapeutic agent than would be necessary in the absence of administration of the nitric oxide donor.

Viral infections that may be treated include those associated with dengue, filoviruses (e.g., Marburg, Ebola), hantaviruses, Hepatitis B, Hepatitis C, Hepatitis E, Human Immunodeficiency viruses (e.g., HIV-1 and HIV-2), human papillomavirus, human T-cell lymphotrophic viruses (e.g., HTLV-1 and HTLV-II), influenza, lassa, measles, monkey pox, Norwalk, rabies, Rift valley, Rotavirus, Venezuelan equine encephalitis, West Nile Virus, and Yellow fever.

Common bacterial infections include pneumonia (*S. pneumoniae*), ear infections (*S. pneumoniae*), diarrhea, urinary tract infections, and skin disorders. Upper respiratory tract infections are caused by Group A streptococci, *Haemophilus influenzae* and the like. Skin infections include impetigo, boils, carbuncles, cellulitis, and complications from burns. Common pathogens include *Staphylococcus aureus*, group A streptococci, *Escherichia coli*, and *Pseudomonas aeruginosa*. Impetigo, a skin infection caused mostly by group A streptococci, can cause severe kidney inflammation, sometimes resulting in kidney failure. Other bacterial species that may result in bacterial infection include species selected from the following: *Escherichia, Pseudomonas, Enterococcus, Proteus, Aerobacter, Bacillus, Clostridium, Xanthomonas, Spirillum, Vibrio, Bacteroides, Klebsiella, Salmonella, Shigella, Erwinia, Ricketssia, Chlamydia, Mycoplasma, Actinomyces, Streptomyces, Mycobacterium, Polyangium, Micrococcus, Lactobacillus, Diplococcus, Streptococcus, Staphylococcus, Spirochaeta, Treponema, Borrelia, Leptospira, Campylobacter, Haemophilus, Legionella, Heliobacter*, and *Neisseria*.

The compositions and methods of the invention are also useful for dental/oral use and for preventing or treating oral bacteria, dental plaque, and periodontal disease, including gingivitis. Thus, the composition may comprise a liquid for use as a mouth rinse or a paste for use to brush teeth. Plaque is a complex structure and is made up of cooperating microbial communities, cellular food debris, carbohydrates and sugars. The bacteria that adhere to the surface of clean teeth secrete a sticky matrix that attracts other bacteria to join the microbial community. Such bacteria include *Streptococcus mutans, S. sobrinus, Actinomyces viscosus, A. naeslundii*, etc. A NO donor can be used with an agent used to remove oral bacteria or plaque to enhance the effects of the anti-plaque agent and as a bactericidal composition. Such anti-plaque agents include but are not limited to thiocyanates, antibiotics including vancomycin and CC10232, bisguanidine antiseptics, including chlorhexidine; quaternary ammonium compounds, including cetylpyridinium chloride, n-alkyl-n-(2-aminoethyl)piperidine, benzethonium chloride, benzalkonium chloride, and cetrimide; organic amine fluorides; stannous fluoride; sodium fluoride; sodium monofluorophosphate; phenolic antiseptics, including menthol, methyl salicylate, and 5-methyl-2-(isopropyl)phenol (thymol); eucalyptol; 1,3-bis(2-ethylhexyl)-5-methyl-1,3-diazinan-5-amine (hexetidine); 2, 4-4'-trichloro-2'-hydroxy diphenyl ether (triclosan); delmopinol; substituted amine alcohols, including octapinol hydrochloride; 5n-octanoyl-3'-trifluormethylsalicylanilide (salifluor); metal ions and salts thereof; sanguinarine; oxygenating agents including hydrogen peroxide, buffered sodium peroxyborate, and peroxycarbonate;

and combinations thereof. See also U.S. Pat. No. 4,590,061 and B. M. Eley, *British Dental J.*, 186, 286-296 (1999).

The invention is also directed to a coating for a medical device, an indwelling medical device, or an implantable medical device. The device may be, but is not limited to, a catheter, prosthesis (e.g. artificial knee, hip, shoulder), fracture fixation device, orthopedic device, intraocular lens, wound dressing, barrier dressing, pacemaker, mechanical heart valve, vascular shunt, vascular graft, artery graft, breast implant, cosmetic implant, cochlear implant, ear drainage tube, dental implant, feeding tube, glaucoma drainage tube, hydrocephalous shunt, keratoprosthesis, left ventricular assist device, nerve guidance tube, ophthalmic drug delivery device, renal dialyzer, stent, tissue adhesive, implantable subcutaneous sensor, and an intravascular sensor.

In one embodiment, the coating comprises one or more nitric oxide donors and one or more therapeutic agents, wherein the nitric oxide donor is a moiety that can donate, release, directly or indirectly transfer, stimulate the endogenous production of, or elevate endogenous levels of, any form of nitrogen monoxide, and wherein the therapeutic agent is a therapeutic protein, including a growth factor, or is a compound for use in treating or preventing bacterial, viral, or microbial infections, or for enhancing wound healing.

The invention also relates to an implantable medical device or medical implant comprising one or more nitric oxide donors and one or more therapeutic agents. In one embodiment, the nitric oxide donor and therapeutic agent are impregnated or entrapped within, or associated with, the medical device or medical implant. In one particular embodiment, the device is made of or coated with elemental silver and a diazeniumdiolate prepared from proline or another small molecule. The device may further comprise a therapeutic agent.

The nitric oxide donor of the invention is a moiety that can donate, release, directly or indirectly transfer, stimulate the endogenous production of, or elevate endogenous levels of, any form of nitrogen monoxide, and the therapeutic agent may be a growth factor or may be a compound for use in treating or preventing bacterial, viral, or microbial infections, or for enhancing wound healing.

Thus, the presently disclosed subject matter relates to the ability of NO to enhance the antimicrobial and/or wound healing ability of other agents, including, but not limited to, topical antimicrobial agents, such as noble metal-containing therapeutics, topical antiseptics, including but not limited to povidone-iodine, betadine, sodium hypochlorite, acetic acid, cationic antiseptics such as hexadecyltrimethylammonium bromine, chlorhexidine, and alkyldimethyl benzyl ammonium chloride, hydrogen peroxide, therapeutic proteins, and topical or systemic antibiotics, including antibiotics from the classes of ansamycins, carbacephem, carbapenems, glycopeptides, monobactams, polypeptides, quinolones, sulfonamides, penicillins, cephalosporins, fluoroquinolones, tetracyclines, macrolides, aminoglycosides, and lincosamides and from the group including clindamycin, erythromycin, tetracycline, metronidazole, mupirocin, fluticasone, bacitracin zinc, neomycin sulfate, and polymyxin B sulfate. Antibiotics also include gentamicin, kanamycin, neomycin, netilmicin, streptomycin, tobramycin, paromomycin, geldanamycin, herbimycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, cefepime, teicoplanin, vancomycin, azithromycin, clarithromycin, cirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, ciprofloxacin, enoxacin, gatifloxacin, levofloxacin, lomeflxacin, moxifloxacin, norfloxacin, ofloxacin, trovafloxacin, mafenide, prontosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincomycin, ethambutol, fusfomycin, fusidic acid, furazolidone, isoniazid, linezoilid, metronidazole, mupirocin, nitrofurantoin, platensimycin, pyrazinamide, quinupristin, dalfopristin, rifampin, rifampicin, tinidazole, etc.

The therapeutic agent may be a topical antiseptic, including but not limited to povidone-iodine, betadine, sodium hypochlorite, acetic acid, cationic antiseptic, and hydrogen peroxide. Antiviral agents include but are not limited to non-nucleoside reverse transcriptase inhibitors, nucleoside reverse transcriptase inhibitors, protease inhibitors, and nucleotide analog reverse transcriptase inhibitors. Therapeutic proteins include enzymes, blood factors, blood clotting factors, insulin, erythropoietin, interferons, including interferon-$\alpha$, interferon-$\beta$, protein C, hirudin, granulocyte-macrophage colony-stimulating factor, somatropin, epidermal growth factor, albumin, hemoglobin, lactoferrin, angiotensin-converting enzyme, glucocerebrosidase, human growth hormone, VEGF, antibodies, and monoclonal antibodies.

Specific growth factors include but are not limited to growth factors selected from families such as transforming growth factor-beta (TGF-$\beta$), bone morphogenic protein (BMP), neurotrophins (NGF, BDNF, and NT3), a fibroblast growth factor (FGF), for example, acidic fibroblast growth factor (aFGF or FGF-1) and basic fibroblast growth factor (bFGF or FGF-2), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), epidermal growth factor (EGF), and hepatocyte growth factor (HGF).

The invention provides means for delivering NO, an unstable gas. The NO can be delivered via NO delivery vehicles such as NO-releasing small molecules (e.g., diazeniumdiolates, proline-derived diazeniumdiolate, S-nitrosothiols, metal coordination complexes, and hydroxyureas, see, for example, Hrabie et al. *Chem. Rev.* 102, 1135-1154 (2002); Want et al., *Chem. Rev.* 102, 1091-1134 (2002), as well as from NO-releasing nanoparticles, microparticles, nano-particle-based scaffolds, and non-particulate polymeric scaffolds. Nano-particle based scaffolds are capable of storing large payloads of NO (see, for example, Rothrock et al., *J. Am. Chem. Soc.* 127, 9362-9363 (2005); Stasko et al., *J. Am. Chem. Soc.* 128, 8265-8271 (2006); Shin et al., *J. Am. Chem. Soc.* 129, 4612-4619 (2007)). Nanoparticles can spontaneously release a predetermined amount of NO under aqueous conditions at physiological temperature and pH. The NO delivery vehicles can be designed to release NO in response to a chemical, electromagnetic (e.g., light-based), or environmental trigger. Such triggers can include enzymatic reactions, photolysis, a transition metal catalyzed reaction, selenium, a change in pH, an electrochemical trigger, a change in temperature, an oxidation reaction, or a reduction reaction. The NO-delivery vehicle can also include a targeting, solubility enhancing or imaging moiety (e.g., a fluorescent group).

With nanoparticle delivery, the rate of NO release can be modulated as a function of nanoparticle size, composition, and/or surface hydrophobicity to provide control over the rate and duration of NO release. Further, the chemistry used to synthesize the nanoparticles allows for specific tailoring of particles with functional groups to minimize their toxicity and evaluate imaging and/or cell specific targeting. See, for example, Rothrock et al. (2005) supra; Stasko et al. (2006) supra; Shin et al. (2007) supra.

In some embodiments, the presently disclosed subject matter relates to synergistic combination therapies involving the administration of a NO donor and a silver-based therapeutic agent, such as silver sulfadiazine (AgSD), silver nitrate, silver bromide, silver sulfate, silver nanoparticles, colloidal silver, or polymers that release or elute silver or silver ion and elemental silver.

The presently disclosed subject matter further relates to methods of enhancing wound healing and/or the treatment or prevention of microbial infections. The presently disclosed subject matter further relates to compositions comprising NO donors and other therapeutic agents for use in treating or preventing microbial infections and for wound healing. The compositions can be formulated for topical administration. Such formulations can take the form of pastes, liquids for oral rinses, creams, gels, salves, foams, aerosols, lotions, ointments, soaps, shampoos, and the like. In some embodiments, the NO donor can be provided in association with a wound dressing, such as a surgical drape, a suture, a bandage, or a gauze. In some embodiments, the NO donor can be impregnated or trapped within, or associated with, a medical device or medical implant or with a coating applied to a medical device or medical implant. Therapeutic agents for use in wound healing include growth factors, compounds for use in treating or preventing bacterial, viral, or microbial infections, or for enhancing wound healing. For the treatment or prevention of microbial infections, the therapeutically active agent will be selected based on the microbial pathogen. Such antimicrobial agents include, but are not limited to topical antimicrobial agents, such as noble metal-containing therapeutics, topical antiseptics, including but not limited to, povidone-iodie, betadine, sodium hypochlorite, acetic acid, cationic antiseptics such as hexadecyltrimethylammonium bromine, chlorhexidine, and alkyldimethyl benzyl ammonium chloride, hydrogen peroxide, and topical or systemic antibiotics such as clindamycin, erythromycin, tetracycline, metronidazole, mupirocin, fluticasone, bacitracin zinc, neomycin sulfate, and polymyxin B sulfate.

As noted, the compositions and methods of the invention can be used in dental applications including for the prevention of oral bacteria and plaque and to treat gum disease. Such therapeutic agents for dental applications include thiocyanates, antibiotics including vancomycin and CC10232, bis-guanidine antiseptics, including chlorhexidine; quaternary ammonium compounds, including cetylpyridinium chloride, n-alkyl-n-(2-aminoethyl)piperidine, benzethonium chloride, benzalkonium chloride, and cetrimide; organic amine fluorides; stannous fluoride; sodium fluoride; sodium monofluorophosphate; phenolic antiseptics, including menthol, methyl salicylate, and 5-methyl-2-(isopropyl)phenol (thymol); eucalyptol; 1,3-bis(2-ethylhexyl)-5-methyl-1,3-diazinan-5-amine (hexetidine); 2, 4-4'-trichloro-2'-hydroxy diphenyl ether (triclosan); delmopinol; substituted amine alcohols, including octapinol hydrochloride; 5n-octanoyl-3'-trifluormethylsalicylanilide (salifluor); metal ions and salts thereof; sanguinarine; oxygenating agents including hydrogen peroxide, buffered sodium peroxyborate, and peroxycarbonate; and combinations thereof.

FIGS. 1-3 are schematic illustrations of some embodiments of compositions that can administer both NO and another therapeutic agent. FIG. 1 illustrates an embodiment related to implantable biomaterial, biomedical implant, or indwelling medical device A that comprises NO-releasing layer B and therapeutic agent-releasing layer C, which releases therapeutic agent X. FIG. 2 illustrates an embodiment related to implantable biomaterial, biomedical implant, or indwelling medical device A' that comprises layer B' which can release both NO and therapeutic agent X. FIG. 3 illustrates composition A" (e.g., a wound dressing, wound barrier, barrier dressing, biomedical implant, a biomaterial, hydrogel, matrix, cream, foam, ointment, or gel) that releases both NO and X.

For topical administration, the therapeutically active compounds can combined with additional materials that are known for use in skin-care products, or which are otherwise suitable for topical application. Such optional materials include, but are not limited to, disbursing agents, masking agents, preservatives, processing agents, and additives having specific physicochemical properties, such as polymeric film formers and the like. The therapeutically active compounds can be administered by any method of delivery known for the therapeutic agent. The therapeutic agent may be delivered within the same composition as the NO donor or may be formulated in a separate composition.

By "enhancing the treatment or prevention of a microbial infection" "enhancing the efficacy of an antimicrobial agent" or "enhancing wound healing" is meant providing any efficacious effect not seen in treatments involving one therapeutic element (e.g., the antimicrobial agent) alone. More particularly, the enhancement can relate to reduced dosage requirements (e.g., when treatment with a combination of an NO donor and an antimicrobial agent has the same effect as treatment with a higher dosage of the antimicrobial agent alone). Enhancement can refer to a reduced likelihood that antimicrobial resistance will occur, reduced treatment times, or the ability to achieve the desired antimicrobial effect by administering a lower dose of therapeutic agent, including but not limited to below the systemic or local toxicity level of the therapeutic agent than would be necessary in the absence of administration of the nitric oxide donor. The terms "synergy" and "synergistic" generally refer to a superadditive effect of a combination therapy. Thus, a "synergistic effect" refers to when a treatment with a combination of two or more therapeutic agents is more effective than would be expected based on adding the therapeutic effects observed with each of the two or more therapeutic agents when administered individually. In some embodiments the synergistic effect is related to a superadditive level of microbicidal activity. In some embodiments, the microbicidal activity is bactericidal activity. In some embodiments, the microbicidal activity is measured for the first two hours following administration of the NO donor and the antimicrobial agent.

"Prevention" when used in reference to a microbial infection can relate to preventing or reducing the incidence of a microbial infection in a subject, to preventing or reducing the recurrence of a microbial infection, or to a combination thereof. Thus, "preventing a microbial infection" can refer to prophylactically treating a subject to lessen the likelihood of occurrence of a microbial infection.

The term "microbial infection" as used herein refers to bacterial and viral infections.

As used herein, the term "antimicrobial agent" refers to any agent that kills, inhibits the growth of, or prevents the growth of a bacteria, a virus, or any microbe. Thus, suitable antimicrobial agents include, but are not limited to, any known antibacterial or antiviral agent or combinations thereof.

"Wound healing" refers to the treatment of any condition where the integrity of tissue is damaged. Wound healing can relate to chronic or acute wounds, wounds in connective tissue and wounds in muscle, bone, and nerve tissue. The wounds may include, but are not limited to the following: surgical wounds; bites; burns; acid and alkali burns; cold burn (frostbite); sun burn; minor cuts, major cuts, abrasions, and lacerations; wounds caused by gunshot or knife injury; wounds caused by congenital disorders; wounds following dental surgery; periodontal disease; wounds following trauma; tumor-associated wounds, which can be classified as malignant cutaneous ulcers related to the primary tumor or metastases; ulcers (including, but not limited to, diabetic ulcers, leg ulcers, foot ulcers); pressure sores; and corneal wounds.

Wounds can be classified by having either an acute or chronic etiology. The method of the present invention may relate to healing one of a chronic wound or an acute wound. Acute wounds are caused by external damage to intact skin and include surgical wounds, bites, burns, cuts and abrasions, as well as more traumatic wounds such as lacerations and those caused by crush or gun shot injuries. Chronic wounds are most frequently caused by endogenous mechanisms associated with a predisposing condition that ultimately compromises the integrity of dermal or epithelial tissue. Pathophysiological abnormalities that may dispose to the formation of chronic wounds such as leg ulcers, foot ulcers, and pressure sores include compromised tissue perfusion as a consequence of impaired arterial supply (peripheral vascular disease) or impaired venous drainage (venous hypertension) and diseases such as diabetes mellitus. Advancing age, obesity, smoking, poor nutrition, and immunosuppression associated with disease (e.g., AIDS) or drugs (e.g., chemotherapy or radiation therapy) may also exacerbate chronic ulceration. Pressure or decubitis ulcers have a different etiology from other chronic wounds in that they are caused by sustained external skin pressure, most commonly in the buttocks, sacrum, and heels.

In some embodiments, "enhancing wound healing" refers to accelerating wound healing. The terms "accelerating wound healing" or "acceleration of wound healing" refer to the increase in the rate of healing, e.g., a reduction in time until complete wound closure occurs or a reduction in time until a % reduction in wound area occurs. Wound healing may be measured by one or more of a rate of complete wound closure, rate of a percentage reduction in wound area, increased rate of re-epithelialization, increase in tissue angiogenesis or vascularization, increase in collagen reorganization, decrease in scar tissue or foreign body capsule formation, decreased or lessened bacterial count, increased length of time without a positive bacterial culture, inflammatory response altered such that wound healing is enhanced, or a modulated immune response deemed beneficial for wound healing.

The terms "treat" or "treatment" as used herein refer to the application or administration of at least one NO donor and at least one therapeutically active agent and where the purpose is to heal, alleviate, ameliorate, or treat a microbial infection or to treat, heal, ameliorate a wound and to promote wound healing.

The term "subject" refers to any organism to which the presently disclosed treatment methods and pharmaceutical compositions can be administered. In specific embodiments, a subject is a mammal. In other embodiments, a subject is a primate, a human, a domestic animal, or an agricultural animal A subject can include a human subject for medical purposes, such as treatment of a condition or disease, or an animal subject for medical, veterinary purposes, or developmental purposes. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Further, a "subject" can include a patient afflicted with or suspected of being afflicted with a condition or disease. Thus, the terms "subject" and "patient" are used interchangeably herein.

The "patient" or "subject" treated in the many embodiments disclosed herein is desirably a human patient, although it is to be understood that the principles of the presently disclosed subject matter indicate that the presently disclosed subject matter is effective with respect to all vertebrate species, including birds and mammals, which are intended to be included in the terms "subject" and "patient." In this context, a mammal is understood to include any mammalian species in which treatment is desirable, particularly agricultural and domestic mammalian species, such as horses, cows, pigs, dogs, and cats.

The compositions of the invention are provided in therapeutically effective amounts. By "therapeutically effective amount" is intended an amount sufficient to inhibit bacterial or viral growth or to enhance wound healing. In the case of NO, a "therapeutically effective amount" is an amount sufficient to enhance the activity of the therapeutic agent. It is recognized that the amount of NO and the therapeutic agent will vary depending upon the therapeutic agent and the intended benefit. One of skill in the art can determine "therapeutically effective amounts" based on the typically administered dosage of the therapeutic agent as well as in vitro activity assays. See the examples included herein. Based on the activity of NO, the amount of therapeutic agent may be decreased or the duration of treatment shortened.

A therapeutically effective amount of a therapeutically active agent within the methods and compositions of the present invention typically ranges from about 1 µg/kg to about 500 mg/kg, about 10 µg/kg to about 500 mg/kg, about 100 µg/kg to about 500 mg/kg, about 1 mg/kg to about 500 mg/kg, about 1 mg/kg to about 400 mg/kg, about 1 mg/kg to about 300 mg/kg, about 1 mg/kg to about 200 mg/kg, about 1 mg/kg to about 100 mg/kg, about 1 mg/kg to about 75 mg/kg, about 1 mg/kg to about 50 mg/kg, or about 1 mg/kg to about 25 mg/kg. In another embodiment, the therapeutically effective dose of a NO donor will depend upon the method of delivery, the type of donor, the storage capacity of the donor, the release rate, and the duration of treatment. The NO donor is designed to deliver a therapeutically effective amount of NO. It has been demonstrated that NO gas (200 ppm for 4 hours) is not toxic to mammalian cells. Thus, using the assays described in the Examples, one of skill can determine the concentration of NO donor to use in a particular therapy.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where the subject is a human subject, the dosage levels can be based upon a body weight of approximately 70 kg. It will be understood, however, that the specific dose level and frequency of dosage for any particular subject may be varied and will depend upon a variety of factors including body weight, age, general health, sex, and diet of the subject, the metabolic stability and length of action of the administered compound, mode and time of administration, rate of excretion, drug combination, and severity of the infection or wound.

The pharmaceutical compositions of the invention may be formulated according to known methods to prepare pharmaceutically useful compositions, and may be administered to a subject by any mode of administration, including oral, topical, nasal, ophthalmic, or parenteral (including intraperitoneal, intravenous, subcutaneous, or intramuscular injection) administration. Suitable formulations and their appropriate carrier vehicles are described, for example, in *Remington's Pharmaceutical Sciences* (18$^{th}$ ed.; Mack Publishing Company, Eaton, Pa., 1990), herein incorporated by reference.

The terms "nitric oxide donor" or "NO donor" refer to species (i.e., a molecule or a portion of a molecule (i.e., a substituent)) that can donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action. A nitric oxide donor may be a small molecule or a NO-releasing macromolecular scaffold.

The terms "nitric oxide-releasing" "NO-releasing" or "nitric oxide-donating" refer to methods of donating, releasing and/or directly or indirectly transferring any of the three redox forms of nitrogen monoxide ($NO^+$, $NO^-$, $NO$). In some cases, the nitric oxide-releasing or donating is accomplished such that the biological activity of the nitrogen monoxide species is expressed at the intended site of action.

The term "NO-releasing small molecule" refers to a small molecule (<500 Daltons) that comprises a NO-donating chemical group. The NO-donating chemical group can be any suitable NO donor, including a nitrate or nitrite donor, or a donor selected from the group consisting of a N-bound or C-bound diazeniumdiolate, a S-nitrosothiol, a metal coordination complex, a hydroxyurea, a nitrosamine, a hydroxyl nitrosamine, and a hydroxylamine.

The term "NO-releasing macromolecular scaffold" refers to an entity having a molecular weight greater than 500 Daltons that comprises one or more NO-donating chemical group and a matrix. The NO-donating chemical group may be associated with the matrix material by means of a covalent linkage, an electrostatic linkage, sequestration within a pore in the matrix material, impregnation or physical entrapment, and loose association with the matrix material. In some embodiments, the NO-releasing macromolecular scaffold refers to a NO-releasing particle (e.g., a nanoparticle, or microparticle), or a non-particulate NO-donating polymeric matrix, such as a NO donating polymer film. The NO-releasing macromolecular scaffold can comprise a matrix material and a NO donor. In some embodiments, the NO-releasing macromolecular scaffold can be a NO-releasing particle such as that described in PCT International Patent Application No. PCT/US06/20781, filed on May 30, 2006, which is incorporated herein by reference in its entirety. The NO-releasing macromolecular scaffold may further comprise the therapeutic agent, which may be an antimicrobial, antibiotic, or antiviral agent or a wound healing agent. The antimicrobial, antibiotic, or antiviral agent or wound healing agent may be associated with the matrix material via a covalent linkage, electrostatic linkage, sequestration within a pore in the matrix material, or may be impregnated, embedded, or physically entrapped within or loosely associated with the matrix material, or coated, deposited, or sputtered onto the matrix surface. The NO-releasing macromolecular scaffold may further comprise one or more of a targeting moiety, a solubility enhancing moiety, or an imaging moiety.

The macromolecular scaffold may comprise a matrix material and the NO donor and/or the therapeutic agent. For example, the NO donor may be incorporated and administered within one macromolecular scaffold, and the therapeutic agent may be incorporated and administered within a separate macromolecular scaffold. Alternatively, the NO donor and the therapeutic agent are contained within the same macromolecular scaffold. In one embodiment, the therapeutic agent may be incorporated within the macromolecular scaffold or attached to the exterior of the scaffold.

The macromolecular scaffold may be formulated into a nanoparticle (See, for example, Gelperina et al., *Am. J. Resp. Crit. Care Med.* 172, 1487-1490 (2005); Müeler et al., *Europ. J. Pharma Biopharma,* 50, 161-177 (2000); Sappinath et al., *J. Cont. Release* 43, 197-212 (2001); Shin et al., *J. Am. Chem. Soc.* 129, 4612-4619 (2007); Luft et al. *Proc. Nat'l. Acad. Sci. USA* 105, 11613-11618 (2008)), a microparticle (See, for example, Ko et al., *Int'l. J. Pharma.* 249, 165-174 (2002); Cleek et al., *J. Cont. Release* 48, 259-268 (1997)), a polymeric film (See, for example, R. Langer, *Science* 249, 1527-1533 (1990)), a hydrogel (See, for example, Lou et al., *J. Cont. Release* 69, 169-184 (2000); West and Hubbell, *Reactive Polymers* 25, 139-147 (1995); R. Langer, *Nature* 392, 5-10 (1998)). Such articles are herein incorporated by reference. See also Hetrick et al., *ACSNano* 2(2), 235-246 (2008), incorporated herein by reference.

The particles of the presently disclosed subject matter can be any shape. Thus, the particles can be spherical, elliptical, or amorphous. The size and shape of the particles is, at least in part, determined by the nature (i.e., the chemical composition) or the method of synthesis of the core. In some embodiments, the size of the particle can be manipulated to affect the amount or rate of NO-release. The rate of NO release may be easily modulated as a function of nanoparticle size, composition, and/or surface hydrophobicity, allowing for control over the duration of NO release. The nanoparticles may be specifically tailored with functional groups to minimize their toxicity and enable imaging and/or cell-specific targeting, while retaining the ability to deliver therapeutic levels of NO.

The term "nanoparticle" is meant to refer to a particle having a diameter of between about 0.5 nm and about 1000 nm. In some embodiments, the nanoparticles have a diameter of between about 1 nm and about 500 nm. In some embodiments, the nanoparticles can have a diameter of between about 2 nm and about 200 nm. In some embodiments, the particles have a diameter of between about 1 nm and about 50 nm.

The term "microparticle" refers to particles having a diameter larger than 1000 nm. In some embodiments, the particles have a diameter of up to about 25 microns. In some embodiments, the particle can have a diameter of up to about 100 microns.

In some embodiments, the macromolecular scaffold can comprise a metallic cluster matrix material. The metallic clusters can comprise any metallic complex that can be passivated or "protected" for further functionalization.

The metallic complexes can be metals, metal alloys, metal salts, or metal oxides. In some embodiments, the metallic complex comprises gold, silver, platinum, iron oxide (i.e., $FeO$, $Fe_2O_3$, or $Fe_3O_4$), or semiconductor particles such as CdSe, and the like. In some embodiments the iron oxide is magnetite (i.e, $Fe_3O_4$). NO-releasing gold nanoparticles have been described in Rothrock, A. R., et al., *J. Am. Chem. Soc.*, 127, 9362-9363 (2005), incorporated herein by reference.

In some embodiments, the matrix material may comprise silver or silver ion or a molecular, compound, particle, or structure containing silver.

In some embodiment, the matrix material is a non-metallic polymer. The polymer may be but is not limited to polypropylenimine, a polyaryl ether, a polypeptide, a polyester, a polyamide, a polyglycerol, a triazine, a methacrylate, polydimethylsiloxane, silicone rubber, silicone elastomer, polyurethane, poly(vinyl chloride), polytetrafluoroethylene, polyethylene, a fluoropolymer, poly(ethylene terephthalate), cellulose, polyacrylonitrile, chitosan, hyaluronic acid, collagen, or a combination thereof. The macromolecular scaffold may comprise a xerogel. The antibacterial activity of NO-releasing xerogel films has recently been described in Hetrick, E. M. and Schoenfisch, M. H., *Biomaterials*, 28 1948-1956 (2007), incorporated herein by reference.

In some embodiments, the polymer is a dendrimer. Dendrimers are polymers with densely branched structures having a large number of reactive groups. A dendritic polymer includes several layers or generations of repeating units which all contain one or more branch points. Dendrimers, including hyperbranched dendritic polymers, are prepared by condensation reactions of monomeric units having at least two reactive groups. Dendrimers generally include terminal surface groups, interior branch junctures having branching functionalities greater than or equal to two, and divalent connectors that covalently connect neighboring branching junctures.

Suitable dendrimers for use as core scaffolds of the presently disclosed particles include polypropylenimine dendrimer; polyamidoamine (PAMAM) dendrimer; polyaryl ether dendrimer; polylysine dendrimer; polyester dendrimer; polyamide dendrimer; dendritic polyglycerol; and triazine dendrimers. See Stasko, N. A., and Schoenfisch, M. H., *J. Am. Chem. Soc.*, 128, 8265-8271 (2006), incorporated herein by reference.

In some embodiments, the matrix material is a co-condensed silica network, such as that formed by the condensation of a mixture of silanes, which can include an alkoxysilane and an aminoalkoxysilane. The macromolecular scaffold may comprise a ceramic silica matrix. NO-releasing silica nanoparticles are described, for example, in Shin, J. H., et al., *J. Am. Chem. Soc.*, 129, 4612-4619 (2007). The aminoalkoxysilane may be charged with NO to form a diazeniumdiolate before or after condensation of the aminoalkoxysilane with the alkoxysilane.

In some embodiments, one or more of the silanes can comprise a Si—X bond, wherein X is a halogen, selected from Cl, Br, F, and I.

As used herein the term "alkoxysilane" refers to a compound comprising one, two, three, or four alkoxy groups bonded to a silicon atom. For example, tetraalkoxysilane refers to $Si(OR)_4$, wherein R is alkyl. The R groups can be the same or different. In some embodiments the alkoxysilane is a tetraalkoxysilane selected from tetramethyl orthosilicate (TMOS) or tetraethyl orthosilicate (TEOS).

In some embodiments, the aminoalkoxysilane has the formula:

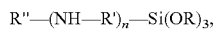
R''—(NH—R')$_n$—Si(OR)$_3$, wherein each R is alkyl; R' is alkylene, branched alkylene, or aralkylene; n is 1 or 2; and R'' is selected from the group consisting of alkyl, cycloalkyl, aryl, and alkylamine In some embodiments, the aminoalkoxysilane can be selected from N-(6-aminohexyl)aminopropyltrimethoxysilane (AHAP3); N-(6-aminoethyl)aminopropyltrimethoxysilane; (3-trimethoxysilylpropyl)di- ethylenetriamine (DET3); (aminoethylaminomethyl)phenethyltrimethoxysilane (AEMP3); [3-(methylamino)propyl]trimethoxysilane; N-butylaminopropyltrimethoxysilane; N-ethylaminoisobutyltrimethoxysilane; N-phenylaminopropyltrimethoxysilane; and N-cyclohexylaminopropyltrimethoxysilane.

In some embodiments, the aminoalkoxysilane has the formula:

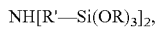
NH[R'—Si(OR)$_3$]$_2$, wherein R is alkyl and R' is alkylene. Thus, in some embodiments the aminoalkoxysilane can be selected from bis-[3-(trimethoxysilyl)propyl]amine and bis-[(3-trimethoxysilyl)propyl]ethylenediamine.

In some embodiments, as described hereinabove, the aminoalkoxysilane is precharged for NO-release and the amino group is substituted by a diazeniumdiolate. Therefore, in some embodiments, the aminoalkoxysilane has the formula:

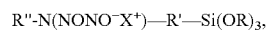
R''-N(NONO$^-$X$^+$)—R'—Si(OR)$_3$, wherein R is alkyl, R' is alkylene or aralkylene, R'' is alkyl or alkylamine, and X' is a cation selected from the group consisting of Na$^+$, K$^+$, and Li$^+$.

The composition of the silica network, (e.g., amount or the chemical composition of the aminoalkoxysilane) and the nitric oxide charging conditions (e.g., the solvent and base) can be varied to optimize the amount and duration of nitric oxide release. Thus, in some embodiments, the composition of the presently disclosed silica particles can be modified to regulate the half-life of NO release from silica particles. In some embodiments, the co-condensed silica network is formed from the condensation of a silane mixture comprising between about 10 mol % and about 99 mol % of alkoxysilane and between about 1 mol % and about 90 mol % of aminoalkoxysilane.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl, "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e.,

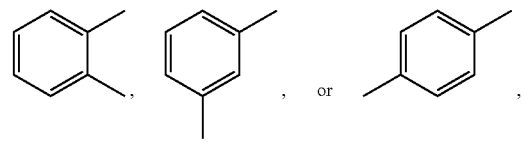

respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-)

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a diazeniumdiolate (i.e., NONO$^-$).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-NH$_2$ group.

The term "silyl" refers to groups comprising silicon atoms (Si).

It will be understood that various details of the presently disclosed subject matter may be changed without departing from the scope of the presently disclosed subject matter.

Furthermore, the foregoing description is for the purpose of illustration only, and not for the purpose of limitation.

The following examples are offered by way of illustration and not by way of limitation.

EXPERIMENTAL

Example 1

Silver Sulfadiazine and Nitric Oxide as Synergistic Biocides

Materials/Methods
General Silver sulfadiazine (AgSD) and proline were purchased from Sigma. Tryptic Soy Broth (TSB) and Tryptic Soy Agar (TSA) were purchased from Difco. L929 cells were obtained from ATCC (ATCC CCL1).
Determining the Minimum Bactericidal Concentration ($MBC_{120}$). Before the synergistic effects of NO and AgSD could be compared, the concentration of each necessary to achieve three logs of killing within 120 min was first obtained. This value, the $MBC_{120}$, was acquired by growing S. aureus to an $OD_{600}$=0.075 in TSB. At this value the concentration was determined to be $10^8$ CFUs/mL. In order to achieve a final bacterial concentration of $10^4$, four ten-fold dilutions were performed in TSB. The bacterial suspension was then immediately added to the proli/NO or the AgSD previously aliquoted into 1.5 mL eppendorf tubes and vortexed for dissolution. For proli/NO, 1 mL of $2\times10^4$ CFUs/mL bacterial solution was added to various masses (0.5-16 mg). For AgSD, 0.5 mL of the bacterial solution was added to 0.5 mL of 2× concentrated AgSD in TSB. Following shaking at 37° C. for the desired time interval, 100 µL of the complete solution was then diluted 1:10 in PBS and 100 µL plated on TSA plates at 0, 30, 60, 90, and 120 min. The plates were incubated overnight at 37° C. and enumerated. The graphs present the total CFUs present in each tube as determined by counting each colony and multiplying that number by 100 to account for both 10-fold dilutions.
Determination of Fractional Bactericidal Concentration ($FBC_{120}$). Time-based synergistic killing assays were performed in (TSB) to test the bactericidal synergy of proli/NO and AgSD. S. aureus was cultured to a concentration of $10^8$ CFUs/mL and the concentration was adjusted to $2\times10^4$ CFUs/mL in TSB. This solution was then added to an equal volume of various concentrations of AgSD in TSB and 1 mL was immediately transferred to eppendorf tubes containing different amounts of proli/NO. The synergistic cocktail was vortexed for 10 s and after fixed time periods (0, 30, 60, 90, 120 min), 100 µL aliquots of the suspension were removed and, after a 10-fold dilution in phosphate buffered saline (PBS), were plated on TSA nutrient plates. After incubating the plates overnight at 37° C., viability was determined by counting the number of distinct colonies on each plate and multiplying this number by 100 to account for the two 10-fold dilutions. The numerical value of the $FBC_{120}$ was obtained according to the equation:

$$FBC_{120} = \frac{MBC_{120AB}}{MBC_{120A}} + \frac{MBC_{120BA}}{MBC_{120B}}$$

L929 propidium iodide (PI) viability assay. L929 cells were plated on 24-well tissue culture treated dishes (BD Bioscience #353047) at a density of $3.0\times10^5$ cells/ml ($150\times10^3$ cells/well) and incubated overnight at 37° C., in 5% $CO_2$/95% air for 18-20 h. For the PI assay, the incubation buffer was aspirated from each of the wells and replaced with 500 µL of Krebs-Ringer-HEPES (KRH) buffer containing (mM): 115 NaCl, 5 KCl, 1 $CaCl_2$, 1 $KH_2PO_4$, 1.2 $MgSO_4$, 25 HEPES, pH 7.4, supplemented with 30 µM of PI. The fluorescence of the cells was determined in a concentration-dependent manner against both proli/NO and proline, as monitored using a FluoStar Galaxy plate reader (BMG Labtech, Durham, N.C.) with excitation and emission filters set at 544 and 640 nm, respectively. Fluorescence was acquired at 0 and 60 min. An additional 20 min incubation of cells with 40 µM digitonin was required to completely permeabilize plasma membranes and achieve maximum PI fluorescence. Cell viability was represented as an increase in PI fluorescence from each well expressed as percentage of the maximum fluorescence obtained in cells treated with digitonin (100% cell death).
S. aureus cytotoxicity assay in PBS. As a means for direct comparison to the L929 PI assay, a bacterial cytotoxicity assay was run in PBS at a concentration of $2\times10^5$ cells/mL, thereby mimicking the concentration and stagnant growth conditions achieved using the KRH buffer. S. aureus was grown to an $OD_{600}$=0.075 and centrifuged for 5 min at 5,000 rpm. The pellet was then resuspended in an equal volume of PBS. This concentration of $10^8$ CFUs/mL was then diluted to $2\times10^5$ CFUs/mL also in PBS. Toxicity was measured by aliquoting this bacterial solution into eppendorf tubes containing proli/NO, incubating these solutions for one hour at 37° C., and then plating them on TSA plates. Colony counts were obtained after an overnight incubation at 37° C.
Results/Discussion
To attempt to develop a combinatorial drug treatment it was first necessary to determine the $MBC_{120}$ for AgSD. Because of the wide range of bacterial concentrations, incubation times, and media compositions used in previous experiments, the value for the MBC of AgSD against S. aureus cannot be clearly defined. See Warriner, R.; Burrell, R., Advances in Skin & Wound Care. 18(Suppl. 1):2-12 (2005). Accordingly it was necessary to determine this value using our experimental method. This result defines the $MBC_{120}$ for AgSD against S. aureus as 175 µg/mL. Also of interest is that increasing the concentration of AgSD to 200 µg/mL decreases the time to achieve complete toxicity by 30 min.

Figure 4:
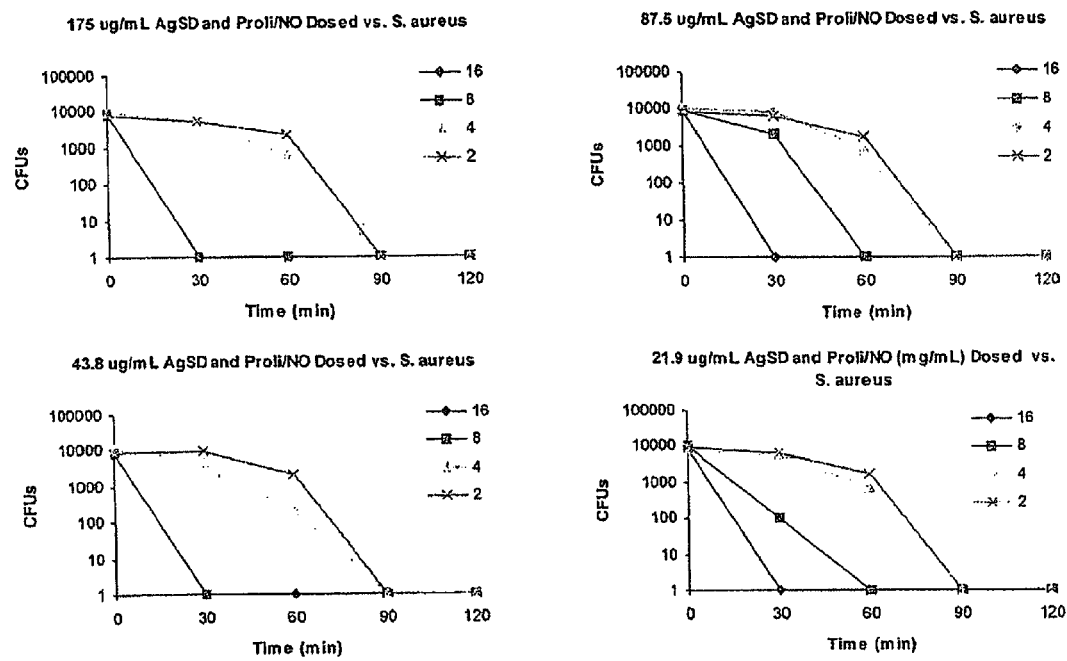
FIG. 4 is a graph showing that the combination of proli/NO AgSD on *S. aureus*. Values are presented in mg/mL, unless otherwise stated. The $FBC_{120}$ is 0.25, since 2 mg/mL, proli/NO (2/16=0.125) and 21.9 µg/mL AgSD (21.9/175=0.125).

Once this value was known, the corresponding value must be obtained for proli/NO, chosen as the model NO donor because of its fast NO release ($t_{1/2}$<2 min) upon exposure to physiological conditions (pH 7.4) and its biocompatible backbone, proline. We synthesized proli/NO by subjecting a 2:1 molar ratio of sodium methoxide in methanol and proline to 5 atm of NO for 3 days. To the resulting solution excess diethyl ether was added. After vacuum removal of solvent a white solid was obtained. Its NO release was monitored using chemiluminescence; we determined that proli/NO releases a total of 1.8 µmol NO/mg in less than 70 s when exposed to PBS at pH 7.4. Release is initiated quickly by protonation of proline's cyclic amine or slowly by thermal degradation. In the $MBC_{120}$ determination, proli/NO was kept on ice until exposure to bacterial solution to prevent thermal NO release. Proli/NO's $MBC_{120}$ is 16 mg/mL against S. aureus. Having demonstrated both compounds' bactericidal properties the next step was to determine if these biocides were synergistic, which we hypothesized/hoped due to the high bioactivity of each compound. A quantitative measure of the synergy between two antibacterial agents has previously been demonstrated via the checkerboard method. See Turner, T. D., et al., J Pharm. Pharmacol. 41, 775-80 (1989). In this procedure, 8 concentrations of antibacterial agent A are compared to 8 concentrations of antibacterial agent B. The range extends from 2× the minimum inhibitory concentration (MIC) to MIC/32, and also a zero concentration of each. Synergy is determined based on inhibition beyond what would be expected for each alone. A similar process was devised to determine the synergy between NO and AgSD in this paper; however, instead of focusing on inhibition of growth we are basing our values on complete toxicity in 120 min. More specifically, the MBC was used instead of the MIC, once again because we are interested in reducing a bacterium's chances of becoming resistant to the drug employed by developing conditions that will lead to a quick kill. Additionally, reducing the bacterial burden in wound beds quickly is paramount to prevent infections. To achieve this end I employed a strategy similar to the FIC, using the $MBC_{120}$ as my maximum value and ending with $MBC_{120}/8$ for both proli/NO and AgSD. As shown in FIG. 4, even at the lowest concentrations of proli/NO and AgSD the combination was an effective bactericide. This data clearly shows the synergistic effects of AgSD and proli/NO. In fact, at an $FBC_{120}$ value of 0.25 this combination is highly synergistic, since any value lower than 0.5 shows synergy. See Feng Q. L. et al., J. Biomed. Mater. Res. 52, 662-668 (2000).

Figure 5:
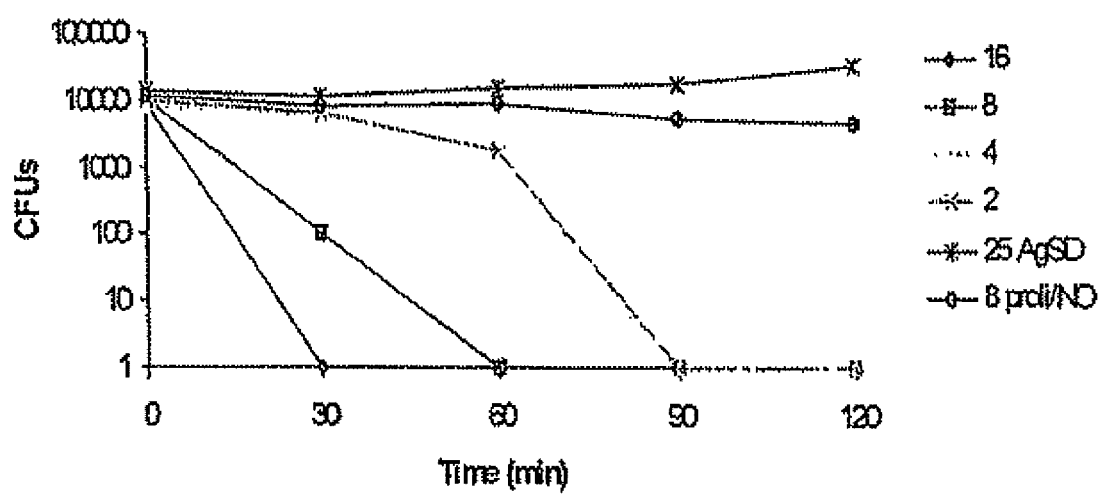
FIG. 5 is a graph showing combined synergy curves showing 16, 8, 4, and 2 mg/mL proli/NO in the presence of 21.9 µg/mL AgSD. For comparison, 25 mg/mL AgSD alone and 8 mg/mL proli/NO alone are also displayed.

FIG. 5 shows the relevant concentrations all on one graph. Specifically, 25 μg/mL of AgSD and 8 mg/mL of proli/NO are both non-toxic alone; however, with the addition of 21.9 μg/mL AgSD even 2 mg/mL proli/NO is effective at inducing complete toxicity.

Since AgSD is commonly used in clinical settings its toxicity against mammalian cells is not a concern; however, NO's potential may be limited by its unknown toxicity against cells most likely to see this drug, dermal fibroblasts. Healthy cells exclude PI from their cytosol, but when cells become injured their membranes become compromised and PI is no longer excluded. By monitoring PI's fluorescence upon binding intracellular nucleic acids it is possible to determine the cell's viability. NO is non-toxic to L929 dermal fibroblasts at concentrations similar to those that were toxic against S. aureus. Note here that the toxicity values obtained for the bacteria are not equal to the values reported above. This is a result of using a cytoxicity assay conducted in PBS, rather than the $MBC_{120}$ in TSB. Because the L929 cells were assayed in KRH buffer rather than growth medium, it was necessary to simulate these conditions in bacteria.

Conclusion. The above results demonstrate that proli/NO can be used at concentrations non-toxic to dermal fibroblasts (2 mg/mL) but still bactericidal towards S. aureus when used in conjunction with sub-inhibitory concentrations of AgSD. Therefore the problem of AgSD resistance can be prevented by simultaneously adding NO. We conclude that sub-inhibitory concentrations of AgSD are lethal within 120 min when used with proli/NO, thereby presenting a proof of concept that bacterial resistance against AgSD can be prevented.

C. Bryce Johnson, Silver Sulfadiazine and Nitric Oxide as Synergistic Biocides, incorporated herein by reference as included in United States Provisional Patent Application Serial No. 60/998,740, filed Oct. 12, 2007.

Example 2

Synthesis and Bactericidal Efficacy of Nitric Oxide-releasing Silica Nanoparticles Characterization of NO-releasing silica nanoparticles and PROLI/NO. Shin et al. previously reported the synthesis and characterization of NO-releasing silica nanoparticles. See Shin, J. H.; Metzger, S. K.; Schoenfisch, M. H., J. Am. Chem. Soc., 129, 4612-4619 (2007). Herein, a slightly modified procedure was followed to improve the NO storage of the silica nanoparticles, whereby the AHAP3 precursors were modified with diazeniumdiolates prior to condensation with TEOS to form the nanoparticles, shown in FIG. 6. The formation of diazeniumdiolate-modified AHAP3 precursors (i.e., AHAP3/NO) prior to co-condensation with TEOS enabled the incorporation of aminoalkoxysilanes up to 45 mol % without aggregation. By forming diazeniumdiolates on the AHAP3 precursor prior to nanoparticle synthesis, particle aggregation was reduced due to decreased hydrogen bonding interactions between amines during particle formation. Additionally, this approach facilitated greater access of sodium methoxide and NO to the amine precursors resulting in ~99% amine-to-diazeniumdiolate conversion efficiency and significantly greater yields of NO per mol of aminoalkoxysilane precursor. To determine whether the presence of sodium methoxide would lead to self-condensation of the AHAP3/NO precursors during the diazeniumdiolate formation step (Step 1 of Scheme 1), $^{29}$Si NMR spectroscopy was employed. Notably, no significant T″ peaks characteristic of organosilane polymerization were observed, indicating that the AHAP3/NO molecules did not pre-condense under such reaction conditions.

Nitric oxide release due to diazeniumdiolate decomposition is initiated by a proton source such as water. The total amount of NO released (t[NO]) from the AHAP3 nanoparticle system was approximately 3.8 μmol NO per mg of nanoparticle while the maximum NO flux ($[NO]_m$) was ~21700 ppb·mg$^{-1}$. The NO release kinetics from the AHAP3 silica nanoparticles were relatively rapid compared to other NO-releasing silica nanoparticle systems, with a NO release half life ($t_{1/2}$) of 18 min. As a result of the rapid NO release from the 45 mol % AHAP3 nanoparticles, the time required to reach the maximum NO flux ($t_m$) of ~21700 ppb·mg$^{-1}$ was only 8 min after immersion in buffer solution. The initial burst of NO allows for the rapid delivery of micromolar quantities of NO that produce the reactive nitrogen and oxygen species that mediate NO's bactericidal actions. As characterized by atomic force microscopy (AFM), the size and homogeneity of the 45 mol % AHAP3 particles were 136±15 nm (Supporting Information). Notably, the size and NO-release properties of diazeniumdiolate-modified silica nanoparticles are tunable based on the amount and identity of aminoalkoxysilane precursor employed in the synthesis.

To facilitate comparison of the bactericidal efficacy of nanoparticle-derived NO with small molecule-derived NO, the amino acid proline was functionalized with diazeniumdiolate NO-donors as described by Saavedra et al. Saavedra, J. E. et al., J. Med. Chem. 39 (22), 4361-4365 (1996). The release of NO from PROLI/NO was also extremely rapid, with a $t_{1/2}$ of approximately 1.7 min. On a per mg basis, PROLI/NO released less than half as much total NO as the AHAP3 nanoparticles, with a t[NO] value of 1.8 μmol NO·mg$^{-1}$. Due to its rapid NO release characteristics, however, the $[NO]_m$ for PROLI/NO (>145000 ppb·mg$^{-1}$) was more than 6 times greater than the $[NO]_m$ generated by the nanoparticles per mg, with $t_m$ approximately 1 min after addition to buffer. Despite the large bolus of NO released by PROLI/NO, the extended duration of NO release from the AHAP3/TEOS nanoparticle system is more beneficial for antibacterial applications because its NO release capabilities are not immediately lost upon exposure to aqueous conditions. Indeed, effective NO-based antibacterial agents require NO release durations long enough to allow the NO donor vehicle to reach the intended site of action without becoming depleted of NO during transit, while still releasing bactericidal quantities of NO.

Bactericidal efficacy under static conditions. The bactericidal efficacy of the 45 mol % AHAP3 NO-releasing silica nanoparticles was evaluated against *P. aeruginosa*, an opportunistic gram-negative pathogen. To determine the influence of the nanodelivery vehicle on the antibacterial properties of NO, the bactericidal efficacy of 45 mol % AHAP3 nanoparticles was compared to that of PROLI/NO. We observed that the diethylenetriamine backbone alone demonstrated considerable toxicity to *P. aeruginosa* (data not shown), which is consistent with the observations of others. Conversely, the backbone of PROLI/NO (the amino acid proline) exhibited no toxicity to *P. aeruginosa* up to 20 mg·mL$^{-1}$, the highest concentrations tested.

To facilitate direct comparison of the amount of NO necessary to kill *P. aeruginosa*, initial studies were conducted in PBS. The bacterial killing assays conducted in aqueous buffer demonstrate the bactericidal activity of NO under nutrient-free ("static") conditions in which the bacteria were unable to replicate. In this manner, the data collected were not convoluted by the ability of the bacterial culture to proliferate in the medium during the experiment. Bacterial killing assays were performed instead of the more conventional minimum inhibitory concentration (MIC) assays in order to assess the extent to which NO actually kills *P. aeruginosa* as opposed to simply inhibiting its growth. An understanding of these parameters is important because it has been suggested that bactericidal agents are less likely to foster resistance among pathogens than those that are simply bacteriostatic. The concentrations of PROLI/NO and NO-releasing nanoparticles that proved completely bactericidal (3 logs of killing) to *P. aeruginosa* were 2.5 mg·mL$^{-1}$ and 70 μg·mL$^{-1}$, respectively. Thus, by mass, approximately 35 times more PROLI/NO was required than silica nanoparticles to completely kill all *P. aeruginosa* cells in the bacterial suspension. Both the proline and 45 mol % AHAP3 silica controls depleted of NO exhibited no killing of *P. aeruginosa* over the concentration ranges tested, indicating that the toxicity observed from the NO-releasing analogues was due entirely to NO. Real-time chemiluminescent detection of NO released from the two NO-donor systems allowed for a direct comparison of the amount of NO released into solution over the 1 h time course of the bactericidal assays. Notably, the amount of NO required per mL to elicit a 3 log reduction in bacterial viability was markedly less from the nanoparticle scaffold than from PROLI/NO (0.22 versus 4.5 μmol NO from nanoparticles and PROLI/NO, respectively). The amount of NO delivered is expressed as total μmol NO released instead of a concentration (e.g., mM) because the NO quickly reacts to form other reactive nitrogen and oxygen species. As such, the exact molar concentration of NO and the byproducts in solution are not known.

Time-based bactericidal assays under nutrient growth conditions. While the PBS-based bactericidal assays allow an uncomplicated comparison of the dose of NO from both systems required to kill *P. aeruginosa*, they do not demonstrate the temporal efficacy of each system, or accurately mimic a situation where the bacteria have the ability to replicate. To better understand such parameters, time-based killing assays were performed in tryptic soy broth (TSB) to test the bactericidal efficacy of NO-releasing silica nanoparticles in a culture medium where the bacterial culture had the capacity to proliferate and present a competition between the rate of bacterial cell killing and replication. Such time-kill studies offer valuable information regarding the temporal efficacy of antimicrobial agents. Conventional antibacterial susceptibility tests such as the MIC and minimum bactericidal concentration (MBC) assays do not allow for acute temporal studies. In the TSB nutrient medium, *P. aeruginosa* exposed to blank and control (proline and silica) solutions proliferated over the 2 h experiment (FIG. 3). As expected, the concentration of both NO-releasing silica nanoparticles and PROLI/NO necessary to completely kill *P. aeruginosa* in TSB was greater than the dose necessary to achieve the same result in PBS. This increase is attributed to both the ability of *P. aeruginosa* to proliferate in TSB and the NO scavenging properties of the protein digest that comprises TSB. Indeed, chemiluminescent NO release measurements performed in TSB revealed that a significant amount of NO was scavenged by the TSB media itself, effectively lowering the amount of NO able to act on the *P. aeruginosa* cells.

Despite the scavenging of NO and bacterial proliferation in TSB, complete bacterial killing was still achieved, albeit at higher concentrations of both nanoparticles and PROLI/NO. Similar to the experiments performed in PBS, the amount (by mass) of PROLI/NO necessary to kill all *P. aeruginosa* was greater than that of NO-releasing nanoparticles. FIG. 3 illustrates the dose- and time-dependent bactericidal activity of both PROLI/NO and NO-releasing silica nanoparticles. At a nanoparticle concentration of 400 μg·mL$^{-1}$, ~90% bactericidal efficacy was achieved after 2 h (one log reduction in viable *P. aeruginosa*). Doubling the particle concentration to 800 μg·mL$^{-1}$ resulted in 100% bacterial killing over the same period (4 log reduction in viable *P. aeruginosa*). Of note, complete bactericidal activity was achieved in a shorter period (90 min) using significantly greater concentrations of silica nanoparticles (3200 μg·mL$^{-1}$). However, particle concentrations >3200 μg·mL$^{-1}$ did not reduce the time necessary for 100% bacterial killing below 90 min (data not shown). In contrast, PROLI/NO achieved more rapid bacterial killing than the 45 mol % AHAP3 nanoparticles, but at significantly greater concentrations. For example, a concentration of 12 mg·mL$^{-1}$ PROLI/NO resulted in complete killing after only 30 min. The difference in the rate of bacterial killing is attributed to the NO-release kinetics of each NO donor. The NO release from PROLI/NO is rapid with a half life ($t_{1/2}$) of 1.7 min, resulting in rapid (<30 min) bacterial killing at 12 and 20 mg·mL$^{-1}$. In contrast, the NO release rate from 45 mol % AHAP3 silica nanoparticles is significantly longer ($t_{1/2}$=18 min), thereby requiring longer incubation periods at 800 and 3200 μg·mL$^{-1}$ to achieve complete bactericidal activity. Analogous to the results obtained in PBS, complete bacterial killing required a markedly greater amount of NO per mL from PROLI/NO (21.6 mmol) than from the NO-releasing silica nanoparticles (2.8 mmol).

A direct comparison of the amount of NO required from each vehicle to achieve 100% bactericidal efficacy in both PBS and TSB is shown in FIG. 4. Greater amounts of NO were necessary in TSB to achieve complete bactericidal activity than from the same vehicles in PBS due to both the ability of *P. aeruginosa* to proliferate in TSB and the NO-scavenging properties of TSB as noted above. Regardless of the media, NO delivered from the nanoparticles exhibited significantly greater bactericidal efficacy than NO delivered from the small molecule diazeniumdiolate (i.e., PROLI/NO). Indeed, the amount of NO required from PROLI/NO to completely kill *P. aeruginosa* was approximately one order or magnitude greater than that required from the 45 mol % AHAP3 nanoparticles. Since the reactivity of NO is largely dependent on its localized concentration and diffusion properties, NO derived from a small molecule dispersed throughout solution may be expected to possess slower diffusion into bacterial cells and correspondingly lessened antibacterial activity compared to the high localized concentrations of NO delivered by silica nanoparticles.

Fluorescein isothiocyanate (FITC)-modified nanoparticles and cellular uptake studies. FITC-modified silica nanoparticles were employed to allow visual observation of nanoparticle interaction with *P. aeruginosa* cells. After synthesis of the nanoparticles, characteristic FITC fluorescence was observed at 500-530 nm when the particles were excited at 488 nm. Incorporation of FITC into the silica nanoparticle scaffold did not significantly alter the NO-release properties of the nanoparticles (data not shown) or the particle diameter (124±13 nm vs. 136±15 nm with and without FITC, respectively). Using the FITC-modified silica nanoparticles, confocal fluorescence microscopy studies were conducted to determine if the enhanced bactericidal efficacy of the NO-releasing silica nanoparticles was due to nanoparticle uptake by *P. aeruginosa* cells. The interaction of the fluorescently-labeled nanoparticles with *P. aeruginosa* cells was monitored at a magnification of 63×. Imaging of progressive focal cross-sections allowed for intracellular particles to be distinguished from particles associated with the surface of the bacterial cells. As shown in FIG. 5, nanoparticles began to accumulate within the *P. aeruginosa* cells as early as 10 min post-injection. The concentration of nanoparticles within the bacterial cells was visibly higher after 20 min, and reached a peak intracellular concentration at 30 min. Beyond 30 min, the intracellular concentration of nanoparticles appeared to subside, potentially due to membrane disruption and/or cell death. Indeed, membrane disruption is a major avenue of NO-based toxicity and is mediated by peroxynitrite, a byproduct of NO's reaction with reactive oxygen species.

Figure 6:
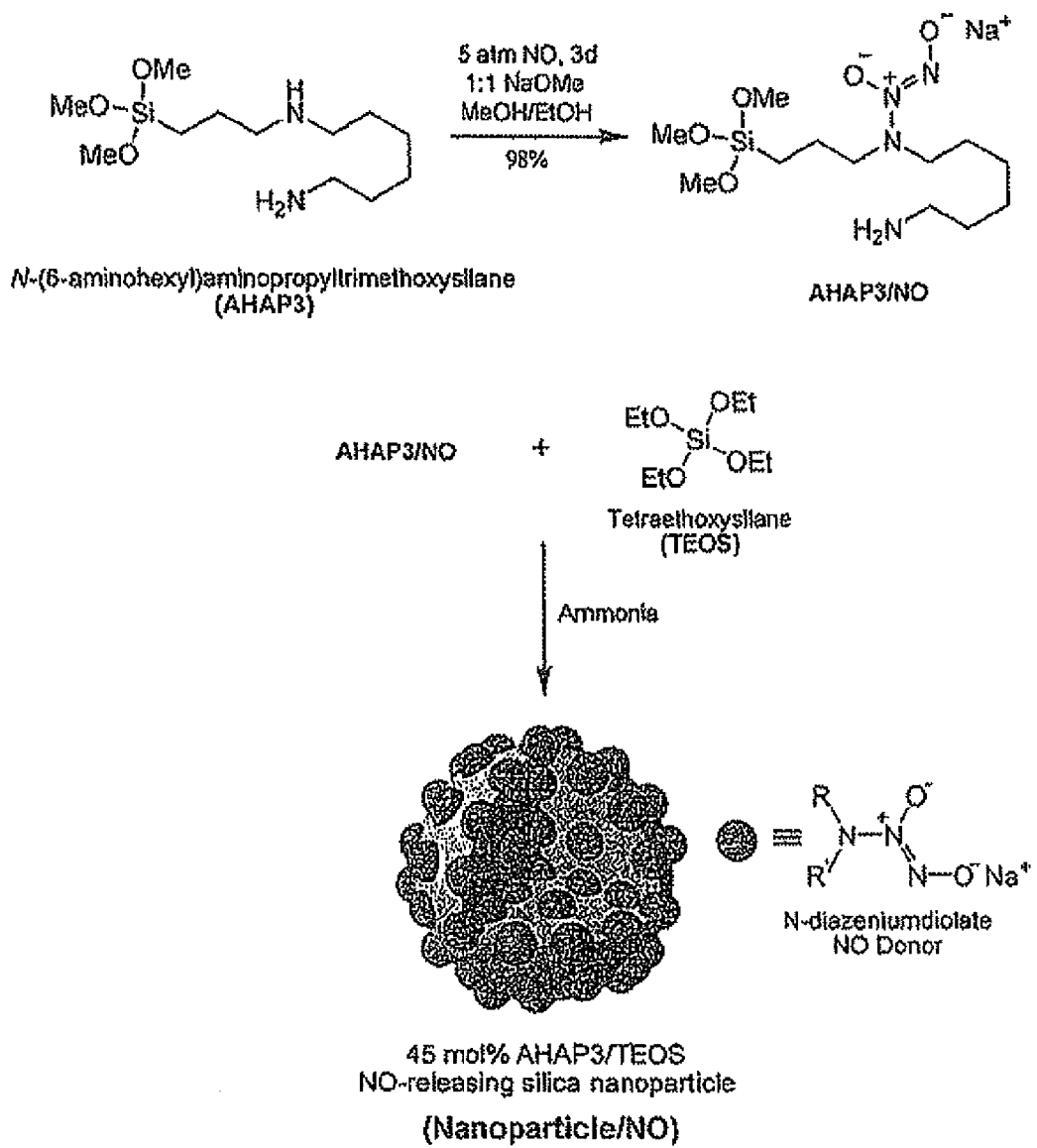
FIG. 6 shows the synthesis of AHAP3 NO donor and co-condensation with TEOS to form NO-releasing silica nanoparticles. $R=(CH_2)_3Si\equiv$ and $R'=(CH_2)_6NH_2$.

The rapid (<30 min) uptake of NO-releasing silica nanoparticles by *P. aeruginosa* may account for their enhanced bactericidal efficacy compared to small molecule NO donors (i.e., PROLI/NO). As shown in FIG. 6, the ability of the nanoparticles to deliver appreciable NO payloads inside bacterial cells allows the NO to more efficiently target intracellular components (e.g., DNA, proteins, enzymes, etc.) critical to cell function, circumventing the need for extracellular NO to diffuse across the cell membrane. The antibacterial properties of NO and its byproducts have been thoroughly reviewed and are typically ascribed to either nitrosative or oxidative stress generated by NO's reactive byproducts. In addition to causing DNA deamination, nitrosative species such as $N_2O_3$ can lead to nitrosation of thiols (S-nitrosation) on proteins, which may directly alter protein function and lead to disulfide bridging with other thiols on the protein. Due to the lipophilic nature of both NO and $O_2$, both species tend to concentrate in cell membranes, thereby accelerating NO's oxidation to $N_2O_3$, which is expected to lead to greater nitrosative stress within and near the bacterial membrane. Nitrosation of both cell surface proteins and intracellular proteins (including enzymes) has been shown to cause bacterial cell death. Oxidative stress is driven primarily by peroxynitrite (ONOO), which forms via the reaction of NO with superoxide endogenously derived from the bacterial cellular respiration process. Thus, oxidative damage is expected to occur predominantly inside the cell, since superoxide does not readily cross cell membranes. A significant antibacterial process related to oxidative stress is peroxynitrite-dependent lipid peroxidation, which stems from OH and $NO_2$ radicals derived from peroxynitrous acid (HOONO; FIG. 7). The production of $NO_2$ radical from NO and $O_2$ is also accelerated in membranes, leading to even greater NO-mediated oxidative stress within bacterial cell membranes.[35] Membrane destruction via lipid peroxidation has been proposed as one of the major mechanisms of NO-mediated bactericidal activity. As a peroxynitrite-dependent process requiring superoxide, NO released inside bacterial cells is expected to exert much greater bactericidal effects than NO release extracellularly. By virtue of the extended NO-release half-life of the silica nanoparticles relative to PROLI/NO, a significant portion of the NO is retained until after uptake by the *P. aeruginosa* cells. Such intracellular NO release may then generate a lethal cocktail of peroxynitrite-mediated oxidative stress inside the bacterial cell enabling maximal damage to occur.

Cytotoxicity of AHAP3 nanoparticles to L929 mouse fibroblasts. The significant toxicity that NO-releasing 45 mol % AHAP3 silica nanoparticles exhibited against *P. aeruginosa* cells demands study of their effect on healthy mammalian cells as well. Studies were conducted to determine the combined effects of NO and the silica nanoparticle scaffold on L929 mouse fibroblast cells. Such cells represent the standard for cytotoxicity testing of novel therapeutic agents. Survival of the L929 cells in the presence of control and NO-releasing silica nanoparticles was monitored via both propidium iodide (PI) and lactate dehydrogenase (LDH) viability assays over 2 h to mimic the time-based bactericidal assays described above. Healthy cells with uncompromised membranes exclude PI in the buffer solution, while disrupted plasma membranes allow PI to diffuse into the cell and emit characteristic fluorescence after complexation with intracellular nucleic acids. Positive detection of LDH in the culture medium also indicates compromised cellular membranes that allow larger proteins to leak out of the cell, further indicating membrane disruption and cell death. Both assays thus monitor membrane permeability to assess cell viability, a suitable method to assay for the destructive properties of reactive NO byproducts that are known to form in greater quantities at lipid membranes. A range of nanoparticle concentrations was tested to encompass the bactericidal concentrations of 45 mol % AHAP3 silica in the PBS and TSB assays (70 µg·mL$^{-1}$ and 800 µg·mL$^{-1}$, respectively). As shown in FIG. 7, both control and NO-releasing 45 mol % AHAP3 silica nanoparticles were found to present minimal toxicity to the L929 fibroblasts. Remarkably, when exposed to the same concentration of NO-releasing silica nanoparticles required to induce 4 logs of bacterial killing (800 µg·mL$^{-1}$; FIG. 3B), L929 cells maintained 92% viability as measured by the PI assay. Thus, *P. aeruginosa* appears to be extremely susceptible to NO-releasing silica nanoparticles, while such delivery vehicles pose minimal threat to healthy mammalian fibroblasts.

Conclusions Nitric oxide derived from silica nanoparticles was shown to be significantly more effective at killing pathogenic *P. aeruginosa* than NO derived from the small molecule NO donor PROLI/NO. While the initial NO release from PROLI/NO is 6-fold greater than from 45 mol % AHAP3 silica nanoparticles, bactericidal assays demonstrated that significantly less NO is actually required from the nanoparticles to kill *P. aeruginosa* than from PROLI/NO. Confirmation of particle uptake by *P. aeruginosa* combined with an understanding of the recently reported mechanisms of NO's antibacterial activity sheds light on the differential toxicity observed between macromolecular and small molecule NO donors. In vitro cytotoxicity experiments conducted with L929 mouse fibroblasts confirmed that NO is largely non-toxic to mammalian fibroblast cells at concentrations capable of killing *P. aeruginosa*. Such results demonstrate the promise that NO holds as a new strategy for battling bacterial infection. In addition, the versatility in the synthesis of NO-releasing silica scaffolds allows for both tuning of size and exterior functionality that may further enhance their use as antibacterial agents. Future studies are aimed at identifying the intracellular location of the reactive radical species formed upon NO release and establishing a mechanistic understanding of the interactions between NO-releasing nanoparticles and bacterial cell membranes. As well, studies are currently planned to evaluate the antibacterial properties of NO-releasing silica nanoparticles against other species of pathogenic bacteria including gram-positive strains and those that exhibit resistance to conventional antibiotics.

Methods

Materials. Tetraethoxysilane (TEOS) and sodium methoxide ($NaOCH_3$) were purchased from Fluka (Bucks, Switzerland). N-(6-Aminohexyl)aminopropyltrimethoxysilane (AHAP3) and 3-aminopropyltrimethoxysilane (APTMS) were purchased from Gelest (Tullytown, Pa.). Methanol (MeOH), ethanol (EtOH), and ammonia solution ($NH_4OH$, 30 wt % in water) were purchased from Fisher Scientific (Fair Lawn, N.J.). Tryptic soy broth (TSB, soybean-casein digest) was purchased from Becton, Dickinson and Company (Sparks, Md.). Nitric oxide (NO, 99.5%) was obtained from Linde (Raleigh, N.C.) and argon (Ar), and nitrogen ($N_2$) gases were purchased from National Welders (Raleigh, N.C.). $P.$ $aeruginosa$ (ATCC #19143) and L929 mouse fibroblast cells were purchased from American Type Culture Collection (Manassas, Va.). Fluorescein isothiocyanate (FITC), proline and reagents for the propidium iodide and lactate dehydrogenase cytotoxicity assays were purchased from Sigma (St. Louis, Mo.). Other solvents and chemicals were analytical-reagent grade and used as received. A Millipore Milli-Q UV Gradient A-10 System (Bedford, Mass.) was used to purify distilled water to a final resistivity of 18.2 MΩ cm and a total organic content of ≦6 ppb.

Synthesis of NO-releasing silica nanoparticles. The synthesis and characterization of NO-releasing silica nanoparticles has been described previously. See Shin, J. H.; Metzger, S. K.; Schoenfisch, M. H., $J. Am. Chem. Soc.$, 129, 4612-4619 (2007), incorporated herein by reference. Briefly, an aminoalkoxysilane solution was prepared by dissolving AHAP3 (2.3 mmol) in 20 mL of EtOH and 4 mL of MeOH in the presence of $NaOCH_3$ (2.3 mmol). The solution was then placed into 10 mL vials equipped with stir bars. The vials were placed in a Parr bottle, connected to an in-house NO reactor, and flushed with Ar six times to remove $O_2$ in the solution. The reaction bottle was pressurized to 5 atm NO for 3 d with continuous stirring of the silane solution. Prior to removing the diazeniumdiolate-modified AHAP3 silane sample (AHAP3/NO), unreacted NO was purged from the chamber with Ar. Silane solutions were prepared by mixing TEOS (2.8 mmol) with AHAP3/NO (2.3 mmol; corresponding to 45 mol %, balance TEOS) for 2 min (Scheme 1). The silane solution was then added into 22 mL of EtOH and 6 mL ammonia catalyst (30 wt % in water), and mixed vigorously for 30 min at 4° C. The precipitated nanoparticles were collected by centrifugation (5000 rpm, 5 min), washed with EtOH several times, dried under ambient conditions for 1 h, and stored in a sealed container at −20° C. until used.

NMR characterization of diazeniumdiolated-modified silane. After removing the AHAP3/NO sample from the NO reaction vessel (after Step 1 of Scheme 1), $^{29}Si$ nuclear magnetic resonance (NMR) spectra were obtained to monitor for any condensation between AHAP3/NO molecules. The cross-polarization/magic angle spinning (CP/MAS) $^{29}Si$ NMR spectra were obtained at 20° C. on a Bruker 360 MHz DMX spectrometer (Billerica, Mass.) equipped with widebore magnets (triple-axis pulsed field gradient double-resonance probes). The alcoholic solution of diazeniumdiolate-modified silane (i.e., AHAP3/NO) was loaded into 4 mm rotors (double-resonance frequency of 71.548 MHz) and spun at a speed of 8.0 kHz. The chemical shifts were determined in ppm relative to a TMS external standard.

Synthesis of fluorescently-labeled NO-releasing silica nanoparticles. Fluorescently-labeled NO-releasing silica nanoparticles were synthesized by modifying a previously reported literature procedure. See Lin, Y.-S. et al., $Chem.$ $Mater.$ 17, 4570-4573 (2005). Briefly, MC (10 μmol) was reacted with APTMS (200 μmol) overnight in the dark to yield FITC-modified silanes. Next, 100 μl of the FITC-modified silane solution was co-condensed with AHAP3/NO (2.3 mmol) and TEOS (2.8 mmol) as described above to yield FITC-labeled NO-releasing silica nanoparticles. Incorporation of FITC was confirmed by exciting the particles at 488 nm and observing the characteristic fluorescence due to FITC at 500-530 nm.

Size characterization of silica nanoparticles. The size of control, NO-releasing, and FITC-modified silica nanoparticles was characterized via atomic force microscopy (AFM). Prior to analysis, the particles were suspended in toluene, deposited on a freshly cleaved mica surface (SPI; West Chester, Pa.), and dried under ambient conditions for 3 h. Contact mode AFM images were obtained in air using a Molecular Force Probe 3D AFM (Asylum Research; Santa Barbara, Calif.) controlled with MFP-3D software running under Igor Pro (Wavemetrics; Lake Oswego, Oreg.). Triangular silicon nitride cantilevers with a nominal spring constant of 0.12 $N \cdot m^{-1}$ and resonance frequency of 20 kHz (Veeco; Santa Barbara, Calif.) were used to acquire height/topography images at a scan rate of 1.0 Hz.

Synthesis of PROLI/NO (adapted from a previously reported procedure). See Saavedra, J. E. et al., $J. Med. Chem.$ 39, (22), 4361-4365 (1996). Proline (300 mg, 2.6 mmol) was dissolved in a 50:50 mixture of methanol:ether and treated with 281 mg (5.2 mmol) of $NaOCH_3$. The basic solution was placed in a glass hydrogenation bomb and stirred. The bomb was copiously flushed with Ar to remove atmospheric $O_2$, followed by introduction of NO gas at 5 atm. After 3 d, the glass vial was removed from the vessel after thorough flushing with Ar. The PROLI/NO solution was treated with cold ether to precipitate the product. The NO donor precipitate was then filtered, and dried under vacuum at −70° C. (dry ice/acetone bath) to yield 299 mg PROLI/NO.

Nitric oxide release measurements. Nitric oxide release from both the diazeniumdiolate-modified silica nanoparticles and PROLI/NO was measured in deoxygenated phosphate-buffered saline (PBS, 0.01 M; 37° C.) at pH 7.4 using a Sievers NOA 280i chemiluminescence NO analyzer (Boulder, Colo.). Nitric oxide released from the donors was transported to the analyzer by a stream of $N_2$ (70 mL·min$^{-1}$) passed through the reaction cell. The instrument was calibrated with air passed through a NO zero filter (0 ppm NO) and a 24.1 ppm NO standard gas (balance $N_2$).

Bactericidal assays under static conditions. To test the bactericidal properties of PROLI/NO and NO-releasing 45 mol % AHAP3/TEOS silica nanoparticles under non-growth ("static") conditions, $P.$ $aeruginosa$ was cultured to a concentration of $10^8$ colony-forming-units (CFUs) per mL in tryptic soy broth (TSB), resuspended in sterile PBS, and adjusted to a concentration of $10^3$ CFU·mL$^{-1}$. Silica nanoparticles (NO-releasing and control), PROLI/NO, and proline were added to separate aliquots of the bacterial suspension over a concentration range optimized for each system. After 1 h incubation at 37° C. with gentle agitation, 100-μL aliquots from each suspension were plated on tryptic soy agar. After overnight incubation at 37° C., the colonies on each plate were counted, allowing for calculation of the number of viable $P.$ $aeruginosa$ cells in each vial at the time of plating.

Time-based bactericidal assays under nutrient growth conditions. To test the temporal efficacy of the NO-releasing silica nanoparticles, time-based antibacterial assays were conducted in TSB nutrient media. *P. aeruginosa* was cultured in TSB to a concentration of $10^8$ CFU·mL$^{-1}$ and diluted to $10^4$ CFU·mL$^{-1}$ in additional TSB. Silica nanoparticles (control and NO-releasing), PROLI/NO, and proline were added to separate aliquots of the $10^4$ bacterial suspension over concentration ranges optimized for each system. Every 30 min for 2 h, 100-µL at aliquots of each suspension were removed, diluted 10-fold in PBS, and plated on tryptic soy agar. Bacterial viability was determined as described above after incubating the plates overnight at 37° C.

Cellular uptake studies. *P. aeruginosa* was cultured in TSB to $10^8$ CFU·mL$^{-1}$, pelleted by centrifugation, resuspended in PBS, and adjusted to a concentration of $10^3$ CFU·mL$^{-1}$ in PBS. The bacterial suspension was seeded onto a glass microscope slide where the bacteria were allowed to adhere for 30 mM. The microscope slide was placed on the stage of a Zeiss LSM 510 confocal fluorescence microscope (Chester, Va.). Prior to the addition of particles, bright-field and fluorescence images of the bacteria were acquired with a 63×N.A. 1.4 planapochromat oil immersion lens. Next, FITC-modified NO-releasing silica nanoparticles (100 µg·mL$^{-1}$) were introduced and bright-field and fluorescence micrographs of the same field were captured after 10, 20, 30, and 60 min. The FITC fluorophores were excited with the 488 nm line of an Ar laser and the fluorescence was collected using a BP500-530 nm bandpass filter. Imaging sequential focal cross-sections allowed for intracellular particles to be distinguished from particles associated with the surface of the bacteria.

Propidium iodide cytotoxicity assay. L929 mouse fibroblasts were plated on 24-well tissue culture treated dishes (BD Bioscience #353047) at a density of $3.0×10^5$ cells·mL$^1$ ($150×10^3$ cells per well) and incubated overnight at 37° C. in 5% $CO_2$/95% air. For the propidium iodide (PI) assay, the incubation buffer (Minimum Essential Medium) was aspirated from each of the wells and replaced with 500 µL of Krebs-Ringer-HEPES (KRH) buffer containing 115 mM NaCl, 5 mM KCl, 1 mM $CaCl_2$, 1 mM $KH_2PO_4$, 1.2 mM $MgSO_4$, 25 mM HEPES, pH 7.4, supplemented with 30 µM PI.[45] Control and NO-releasing silica nanoparticles were added to the wells at 0, 50, 200, 400, 600, 800, or 1000 µg·mL$^{-1}$. The fluorescence resulting from PI complexation with intracellular nucleic acid material[43] in cells with compromised membranes was acquired at 15 min intervals for a total of 120 min. Upon completion of these measurements, the cells were incubated with digitonin (40 µM) for 20 min to completely permeabilize the plasma membranes and achieve a maximum PI fluorescence. Cell viability is presented as the increase in PI fluorescence from each well expressed as the percentage of maximal fluorescence obtained from cells treated with digitonin (100% cell death).

Lactate dehydrogenase cytotoxicity assay. The lactate dehydrogenase (LDH) cytotoxicity assay was performed concomitantly with the same cells used for the PI assay described above. Every 15 mM, 20-µL aliquots of KRH buffer were removed from the plate used for the PI assay and stored at −20° C. in black 96-well plates (Greiner; Monroe, N.C.) for subsequent LDH analysis. The 96-well plates containing aliquots of incubation buffer were warmed to 37° C. Lactate dehydrogenase activity was measured from the rate of NADH production after adding 180 µL of KRH buffer containing 0.22 mM NAD$^+$, 11.1 mM sodium lactate and 11.1 mM hydrazine, pH 8.0 into each well.[46] The NADH fluorescence was monitored with a FluoStar Galaxy plate reader using 340 nm excitation and 460 nm emission filters. The LDH activity is expressed as the change in relative fluorescence per min per well. The data are normalized to maximal LDH activity in each well obtained from samples treated with 40 µM digitonin for 20 min.

Statistics. For the bactericidal assays conducted in PBS, n=3 and data are expressed as mean values±standard deviation. Data from both the PI and LDH cytotoxicity assays are presented as mean values±standard error of the mean. See United States Provisional Patent Application Serial No. 60/998,740, filed Oct. 12, 2007, incorporated herein by reference.

Example 3

Confocal Microscopy Studies Evaluating the Bactericidal Efficacy of No Delivered from Nanoparticles as Compared to PROLI/NO To better understand the enhanced bactericidal efficacy of NO delivered from nanoparticles compared to PROLI/NO, fluorescein isothiocyanate (FITC)-modified silica nanoparticles were synthesized to visually determine if any nanoparticle interaction with *P. aeruginosa* cells existed. After synthesis of the nanoparticles, characteristic MC fluorescence was observed at 500-530 nm when the particles were excited at 488 nm. Incorporation of FITC into the silica nanoparticle scaffold did not significantly alter the NO-release properties of the nanoparticles (data not shown) or the particle diameter (124±13 nm vs 136±15 nm with and without FITC, respectively). With the FITC-modified silica nanoparticles, confocal fluorescence microscopy studies were conducted to determine if the enhanced bactericidal efficacy of the nanoparticles was due to nanoparticle interaction with *P. aeruginosa* cells. Nanoparticles began to associate with the *P. aeruginosa* cells as early as 10 min post-injection. The possible mechanism by which this association occurs is not entirely understood but most likely is attributed to electrostatic and/or hydrophobic interactions between the particles and bacterial membrane.

A NO-sensitive fluorescence probe, 4,5-diaminofluorescein dieacetate (DAF-2 DA) was used to determine if the association between NO-releasing silica nanoparticles and *P. aeruginosa*, an opportunistic Gram-negative pathogen, resulted in high local concentrations of NO and more efficient delivery of NO to the bacterial cells. Once inside the bacterial cell membrane, the DAF-2 DA probe is hydrolyzed to DAF-2, which is membrane-impermeable. In the presence of NO, DAF-2 is nitrosated by reactive nitrogen species and exhibits green intracellular fluorescence. Cells loaded with DAF-2 were imaged in the presence of propidium iodide (PI), which is a nucleic acid viability dye that only enters cells with compromised membranes, and fluoresces red once inside the cells. Thus, red fluorescence is indicative of cell death. *P. aeruginosa* cells loaded with DAF-2 exposed to 100 µg·mL$^{-1}$ NO-releasing nanoparticles exhibited strong DAF-2 fluorescence, indicating a high localized concentration of NO in close proximity to the bacterial cells. The DAF-2 fluorescence increased progressively as more NO was released from the nanoparticles, indicating that the NO level in each cell was increasing. After a peak intracellular intensity of DAF-2 fluorescence was reached, the red fluorescence of the PI began to increase, indicating entry of the PI into the cells due to membrane disruption and cell death. The increase in PI fluorescence coincided with a decrease in DAF-2 fluorescence, suggesting that the DAF-2 fluorophore leaked from the cytosol through the damaged cell membrane that allowed the PI to enter the cells.

In contrast to the strong intracellular green fluorescence observed from DAF-2 in the presence of 100 µg·mL$^{-1}$ NO-releasing silica nanoparticles, no intracellular DAF-2 fluorescence was observed when an equal amount of NO was delivered with PROLI/NO. As indicated by the absence of any PI fluorescence from the bacterial cells over the same period, P. aeruginosa cell death was not observed with this dose of NO from PROLI/NO, thus reaffirming that doses of NO delivered from nanoparticle delivery vehicles were more efficient at killing P. aeruginosa cells compared to similar doses from small molecule NO donors. When the amount of PROLI/NO was increased to bactericidal levels (5 mg·mL$^{-1}$), rapid cell death was observed as evidenced by bright red intracellular PI fluorescence in the confocal microscopy images. However, intracellular DAF-2 fluorescence was still not observed prior to cell death (in contrast to the nanoparticles), indicating that the NO concentration surrounding the cells was not high enough to induce intracellular DAF-2 fluorescence. These data reveal that the delivery of NO P. aeruginosa is significantly more efficient from silica nanoparticles than from PROLI/NO. As such, lower doses of NO delivered from silica nanoparticles effectively kill the bacteria.

The ability of the nanoparticles to deliver appreciable NO payloads in close proximity to the bacterial cells allows the NO to more efficiently target cellular components (e.g., cell membrane, DNA, proteins, etc.) critical to cell function, circumventing the need for NO to diffuse across large distances in solution to reach the cell. As a lipophilic molecule, NO is capable of rapidly crossing cell membranes. The release of high levels of NO at or near the cell membrane would be expected to lead to high intracellular concentrations of NO.

Membrane destruction via lipid peroxidation has been proposed as one of the major mechanisms of NO-mediated bactericidal activity. As a peroxynitrite-dependent process requiring superoxide, NO released in close proximity to a bactericidal cell would be expected to exert greater bactericidal effects than NO released diffusely throughout solution by generating a larger intracellular NO concentration. Indeed, we observed direct evidence of membrane destruction during the confocal microscopy experiments by the rapid appearance of intracellular PI fluorescence in cells treated with NO-releasing silica nanoparticles. By virtue of the extended NO-release half-life of the silica nanoparticles relative to PROLI/NO, a significant portion of the NO is retained until after particle association with the P. aeruginosa cells. Such high localized NO release in close proximity to the bacterial cells may then facilitate delivery of greater concentrations of NO and other reactive species to the cell membrane and into the cell itself, leading to enhanced bactericidal efficacy of NO delivered from nanoparticles.

See Hetrick et al., ACSNano 2(2), 235-246 (2008), incorporated herein by reference.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A pharmaceutical composition comprising a NO donor and a silver-based therapeutic agent, wherein the NO donor comprises a NO-releasing macromolecular scaffold and wherein the NO-releasing macromolecular scaffold is a nanoparticle or microparticle comprising a matrix material that releases nitric oxide, wherein said matrix material comprises a co-condensed silica network and said silver-based therapeutic agent is selected from the group consisting of silver sulfadiazine, silver nitrate, silver bromide, silver sulfate and combinations thereof, and wherein the NO donor and the silver-based therapeutic agent exhibit a superadditive effect wherein the combination of the NO donor and the silver-based therapeutic agent is more effective than would be expected based on adding the therapeutic effects observed with the NO donor and silver-based therapeutic agent individually.

2. The pharmaceutical composition of claim 1, wherein said silver-based therapeutic agent is silver sulfadiazine.

3. The pharmaceutical composition of claim 1, wherein said NO donor comprises a compound containing a functional group selected from the group consisting of diazenium diolates, S-nitrosothiols, metal coordination complexes, hydroxyureas, nitrosamines, hydroxyl nitrosamines, and hydroxyl amines.

4. The pharmaceutical composition of claim 1, wherein the silver-based therapeutic agent is either incorporated into the NO-releasing macromolecular scaffold or attached to the exterior of the scaffold.

5. The pharmaceutical composition of claim 1, wherein the NO donor is associated with the matrix material by means of an association selected from the group consisting of a covalent linkage, an electrostatic linkage, sequestration within a pore in the matrix material, impregnation or physical entrapment, and loose association with the matrix material.

6. The pharmaceutical composition of claim 1, wherein the NO donor donates, releases, or transfers a form of nitrogen monoxide in response to the introduction of a trigger selected from the group consisting of an enzyme, protein, or other biological factor; a transition metal, transition metal ion, or transition metal complex; a selenium catalyst; a copper catalyst; a compound containing a thiol group; electromagnetic radiation; a change in pH; an electrochemical signal; a change in temperature; an oxidation reaction; and a reduction reaction.

7. The pharmaceutical composition of claim 1, wherein said composition is formulated for topical, intravenous, oral, intraparenteral, intravaginal, intraocular, transbuccal, transmucosal, or transdermal administration.

8. The pharmaceutical composition of claim 1, wherein said NO donor provides a maximum NO flux of at least about 21,700 ppb/mg upon exposure to physiological conditions.

9. The pharmaceutical composition of claim 1, wherein the NO donor comprises diazeniumdiolate-functionalized proline.

10. The pharmaceutical composition of claim 1, wherein the pharmaceutical composition provides one or more of:
   an antimicrobial activity similar to or greater than that related to administration of a higher dosage of the silver-based therapeutic agent in the absence of administration of the NO donor;
   a reduced likelihood of antimicrobial resistance developing to the silver-based therapeutic agent; and
   the ability to achieve the desired antimicrobial effect by administering a lower dose of the silver-based therapeutic agent, including but not limited to below the systemic or local toxicity level of the silver-based therapeutic agent than would be necessary in the absence of administration of the NO donor.

11. The pharmaceutical composition of claim 1, wherein the NO donor or the silver-based therapeutic agent is present in a sub-bactericidal concentration.

12. The pharmaceutical composition of claim 1, wherein the NO donor and the silver-based therapeutic agent are present in a sub-bactericidal concentration.

13. The pharmaceutical composition of claim 1, wherein the NO donor or the silver-based therapeutic agent is present in a sub-inhibitory concentration.

14. The pharmaceutical composition of claim 1, wherein the NO donor and the silver-based therapeutic agent are present in a sub-inhibitory concentration.

15. The pharmaceutical composition of claim 1, wherein the NO donor and the silver-based therapeutic agent are present in a concentration less than a concentration that provides a 3 log microbial kill in 120 minutes ($MBC_{120}$).

16. The pharmaceutical composition of claim 1, wherein the NO donor and the silver-based therapeutic agent provide a fractional bactericidal concentration (FBC) of 0.5 or less.

17. A pharmaceutical composition comprising a NO donor and a silver-based therapeutic agent, wherein the NO donor comprises a NO-releasing macromolecular scaffold and wherein the NO-releasing macromolecular scaffold is a nanoparticle or microparticle comprising a matrix material that releases nitric oxide, wherein said matrix material comprises a co-condensed silica network and said silver-based therapeutic agent is selected from the group consisting of silver sulfadiazine, silver nitrate, silver bromide, silver sulfate and combinations thereof, and wherein the NO donor and the silver-based therapeutic agent are present in a concentration less than a concentration that provides a 3 log microbial kill in 120 minutes ($MBC_{120}$) and in combination provide a fractional bactericidal concentration (FBC) of 0.5 or less.

18. The pharmaceutical composition of claim 17, wherein each of said silver-based therapeutic and said NO donor is applied in a separate composition to form said composition.

19. The pharmaceutical composition of claim 1, wherein each of said silver-based therapeutic and said NO donor is applied in a separate composition to form said composition.

* * * * *

UNITED STATES PATENT AND TRADEMARK OFFICE
CERTIFICATE OF CORRECTION

PATENT NO.        : 8,399,005 B2                                      Page 1 of 1
APPLICATION NO. : 12/682305
DATED             : March 19, 2013
INVENTOR(S)       : Schoenfisch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this
First Day of September, 2015

Michelle K. Lee
*Director of the United States Patent and Trademark Office*